US008038668B2

(12) United States Patent
Scott et al.

(10) Patent No.: US 8,038,668 B2
(45) Date of Patent: Oct. 18, 2011

(54) CRYOSURGICAL DEVICE AND METHOD FOR COOLING SURFACES

(75) Inventors: John W. Scott, Perkasie, PA (US); William Eric Ross, Long Valley, NJ (US); Philip Michael Formica, Center Valley, PA (US); Keith W. Kardos, Bethlehem, PA (US); Daniel Gary Shenberger, Allentown, PA (US); David Schiff, Highland Park, NJ (US); Peter Byar, Willingboro, NJ (US)

(73) Assignee: Orasure Technologies, Inc., Bethlehem, PA (US)

( * ) Notice: Subject to any disclaimer, the term of this patent is extended or adjusted under 35 U.S.C. 154(b) by 0 days.

(21) Appl. No.: 11/227,204

(22) Filed: Sep. 16, 2005

(65) Prior Publication Data

US 2006/0116670 A1  Jun. 1, 2006

Related U.S. Application Data

(60) Provisional application No. 60/672,506, filed on Apr. 19, 2005, provisional application No. 60/610,534, filed on Sep. 17, 2004.

(51) Int. Cl.
*A61B 18/02* (2006.01)
(52) U.S. Cl. ............... 606/22; 606/20; 606/21; 606/23; 606/28; 222/3; 222/108; 222/111; 222/153.01; 222/153.13; 222/402.11
(58) Field of Classification Search ............. 606/20–26; 222/3, 153.01–153.13, 402.11, 108, 111
See application file for complete search history.

(56) References Cited

U.S. PATENT DOCUMENTS

| 3,768,475 A | * | 10/1973 | Osborne ............... 604/249 |
| 4,211,231 A | | 7/1980 | Rzasa |
| 4,865,230 A | * | 9/1989 | Tugwood ............ 222/383.3 |
| 5,018,647 A | * | 5/1991 | Abplanalf ............... 222/108 |
| 5,042,261 A | | 8/1991 | Yeakel et al. |
| 5,947,960 A | | 9/1999 | Griswold |
| 6,387,090 B1 | | 5/2002 | Jensma |

FOREIGN PATENT DOCUMENTS

| EP | 0 420 561 A1 | 4/1991 |
| GB | 1163573 | 9/1969 |

OTHER PUBLICATIONS

International Search Report dated Dec. 12, 2005.

* cited by examiner

*Primary Examiner* — Sam Yao
*Assistant Examiner* — Aaron Roane
(74) *Attorney, Agent, or Firm* — J.A. Lindeman & Co., PLLC

(57) ABSTRACT

A cryosurgery device for dispensing a liquid refrigerant from a container having a valve stem extending outwardly therefrom. The device includes an actuator adapted to seat on the valve stem of the container in order to depress the valve stem to release the refrigerant from the container. The actuator includes an inner passageway having opposed ends disposed therein, one of the ends of the passageway being in fluid communication with the valve stem. An applicator tube is mounted to the actuator at the other end of the inner passageway. A cap is disposed on the top of the container. The actuator is movably positioned on the cap and a shield is attached to the cap to completely receiving the applicator tube. Liquid refrigerant can only be dispensed when the actuator is positioned properly and the applicator tube is disposed within the shield means.

24 Claims, 24 Drawing Sheets

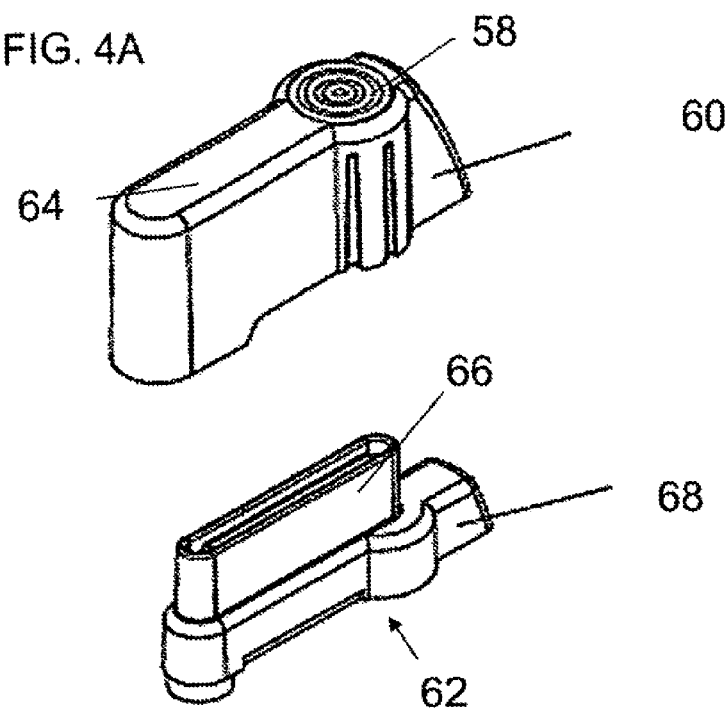
FIG. 4A
FIG. 4B
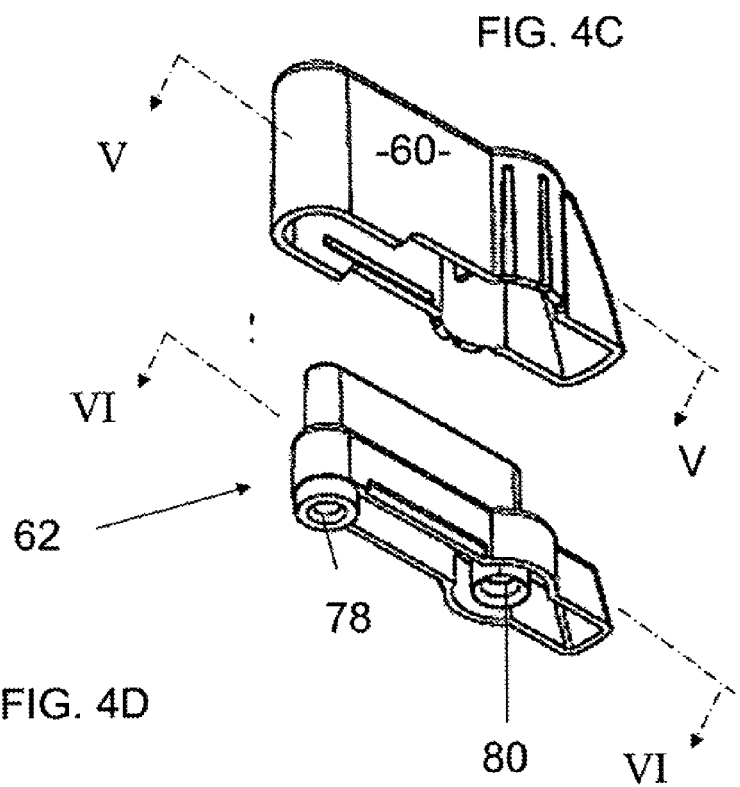
FIG. 4C
FIG. 4D

FIG. 5A
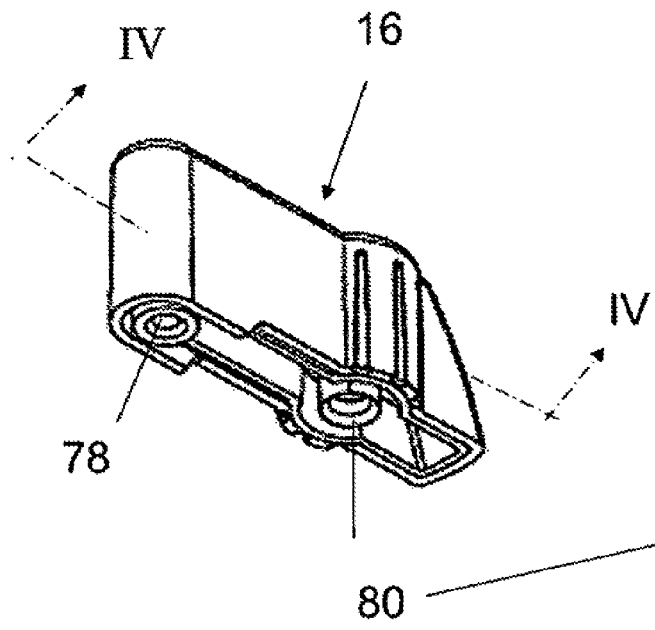
FIG. 5B
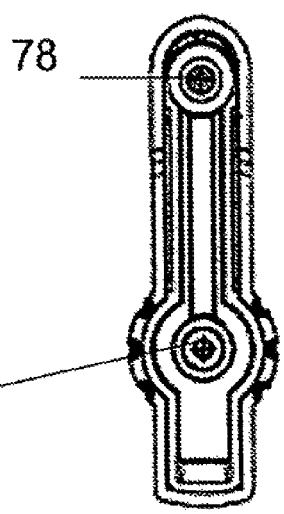
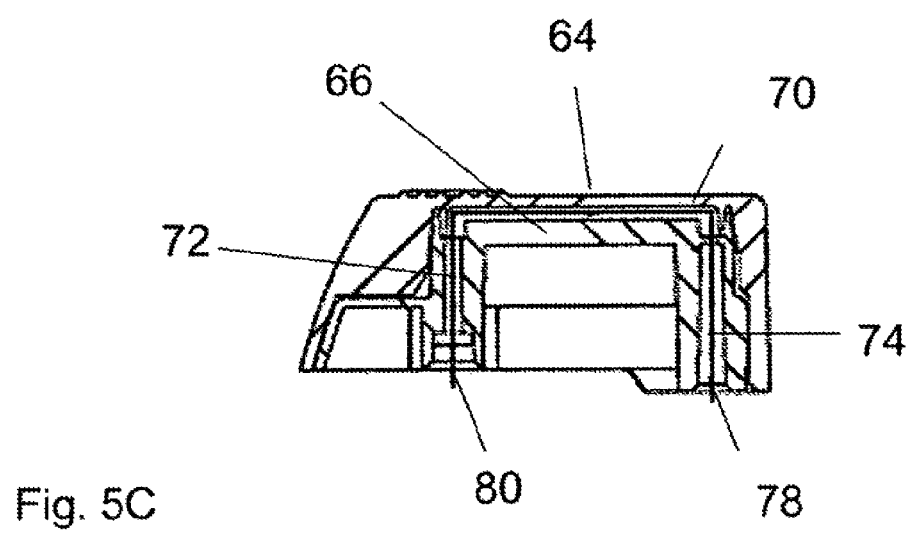
Fig. 5C

CRYOSURGICAL DEVICE AND METHOD FOR COOLING SURFACES

RELATED APPLICATIONS

This application claims priority under 35 U.S.C. §119 to U.S. Provisional Application Ser. Nos. 60/672,506 filed Apr. 19, 2005 and 60/610,534 filed Sep. 17, 2004, which are both incorporated herein by reference.

BACKGROUND OF THE INVENTION

1. Field of the Invention

The invention relates to a cryosurgical device and method for cooling surfaces by dispensing a liquid refrigerant through a shaped applicator of porous material, and more particularly, to a device having a dispensing system with a protective sheath such that refrigerant can only be discharged when the device is correctly assembled.

2. Description of the Related Art

It is known to provide localized freezing of a part of a human or animal body in order to remove a skin lesion such as a wart. Physicians have used liquid nitrogen applications to remove lesions from the skin. This method of treatment has been effective but suffers from the disadvantage of requiring specialized equipment to condense nitrogen, the need for specialized storage devices, and the inherent hazards of handling and dispensing a material having a boiling point of approximately −196° C. A certain amount of skill is required during treatment, so that excessive tissue injury does not occur.

More recently, methods were developed to treat skin lesions cryogenically by employing a liquid refrigerant contained in a pressurized container. In such methods, an effective amount of the cryogenic agent from the pressurized container is supplied into a hollow supply tube, having a cotton, fiber or plastic foam applicator located at the distal end of the tube, so that the cryogenic material accumulates in the applicator. The skin surface of the lesion is then contacted with the applicator having the accumulated cryogenic agent for a period of time sufficient to permit the cryogenic agent to reduce the temperature of the skin lesion tissue to temperatures that freeze the skin, such that permanent, irreversible rupture of cellular membranes of cells of the skin lesion occurs while the cryogenic agent is evaporating. Subsequently, the applicator is removed from the skin surface after a period of time that is generally about 20 to about 60 seconds, depending on the boiling point of the refrigerant and the depth of tissue that will be frozen, and the frozen skin tissue of the skin lesion is then permitted to slowly thaw. During the next several weeks, the tissue that was frozen dislodges from the surrounding skin.

Examples of devices for applying a cryogenic agent to a skin lesion are disclosed in U.S. Pat. No. 4,865,028 (Swart); U.S. Pat. No. 5,516,505 (McDow); U.S. Pat. No. 5,200,170 (McDow); U.S. Pat. No. 5,330,745 (McDow); U.S. Pat. No. 5,738,682 (Jensma); U.S. Pat. No. 6,296,410 (Ruizendaal); U.S. Pat. No. 6,092,527 (Jensma); U.S. Pat. No. 6,296,410 (Ruizendaal); U.S. Pat. No. 6,387,090 (Jensma); and U.S. Published Patent Application No. 2005/0043723 (Howlett et al.). The disclosures of these patents and application are herein incorporated by reference. U.S. Pat. No. 4,865,028 discloses a method and apparatus for delivering a therapeutic effect by delivering refrigerant through an applicator comprising a cotton wool bud surrounding the discharge end of the outlet of a tube and which is placed directly on or near the site to be treated. U.S. Pat. Nos. 6,092,527, 6,387,090 and 5,738,682 disclose a method and apparatus for providing a localized freezing of a wart or other growth. The Jensma patents disclose a shaped applicator tip composed of open celled foam and particularly an applicator comprised of open celled foam over cotton which is preferred for use in the present invention.

An operational feature of cryosurgical devices is the manner in which the cryogenic agent is moved from the container to the applicator. There should be little loss in the cryogenic material during transfer and, therefore, the cryogenic material should travel the most effective and shortest path in order to provide the greatest effectiveness in treating the skin lesion.

SUMMARY OF THE INVENTION

The present invention provides a cryosurgery device for applying a cryogenic refrigerant to or near a skin lesion that provides an accurate and controlled supply of the cryogenic refrigerant.

The present invention still further relates to a dispensing system wherein excess cryogen is held within a reservoir to avoid excess saturation of the applicator tip. The excess reservoir contains the excess cryogen and can show when the applicator has been adequately charged and can retain cryogen if the applicator is not present.

The cryosurgery device of the present invention also provides for applying a cryogenic refrigerant to or near a skin lesion in which the cryogenic material travels an effective and short path to the applicator tip.

The present invention further provides a cryosurgery device for applying a cryogenic refrigerant to or near a skin lesion that is economical to manufacture and easy to use by consumers.

In accordance with the present invention, there is provided a cryosurgery device for dispensing a liquid refrigerant from a container having a valve stem extending outwardly therefrom. The device includes an actuator adapted to seat on the valve stem of the container in order to depress the valve stem to release the refrigerant from the container. The actuator includes an inner passageway having opposed ends disposed therein, one of the ends of the passageway being in fluid communication with the valve stem. An applicator is mounted to the actuator at the other end of the inner passageway. Shield means in communication with the actuator completely receive the applicator. Means interlock the actuator and shield means so that the liquid refrigerant can only be dispensed into the applicator when said actuator engages said shield means.

The present invention further provides a method of dispensing liquid refrigerant from a cryosurgery device comprising the steps of providing a container of liquid refrigerant having a valve stem extending outwardly therefrom. An actuator mechanism is attached to the container, the actuator mechanism including an inner passageway in fluid communication with the valve stem and an applicator. The applicator is positioned within a shield device. The actuator and shield device are interlocked, such that when the actuator mechanism is actuated refrigerant passes from the valve stem through the actuator and into the applicator when a force is applied to the actuator to dispense the refrigerant to the applicator.

These and other features, aspects, and advantages of the present invention will become more apparent from the following detailed description of the preferred embodiment relative to the accompanied drawings, in which:

BRIEF DESCRIPTION OF THE DRAWINGS

FIGS. 4A-4D are perspective views of the shell and insert of the actuator assembly in an unassembled state.

FIG. 5A is a perspective view of the shell and insert assembled as the actuator assembly, FIG. 5B is a bottom view of the actuator assembly of FIG. 5A, and FIG. 5C is a cross-sectional view of the actuator assembly taken along line IV-IV of FIG. 5A.

DETAILED DESCRIPTION OF THE PREFERRED EMBODIMENTS

The present invention relates to a cryosurgical device and method for cooling surfaces by dispensing a liquid refrigerant through a shaped applicator of porous material. The device has a dispensing system with a protective sheath such that refrigerant can only be discharged when the device is correctly assembled. Where possible, like numerals have been used to designate like elements.

Figure 1:
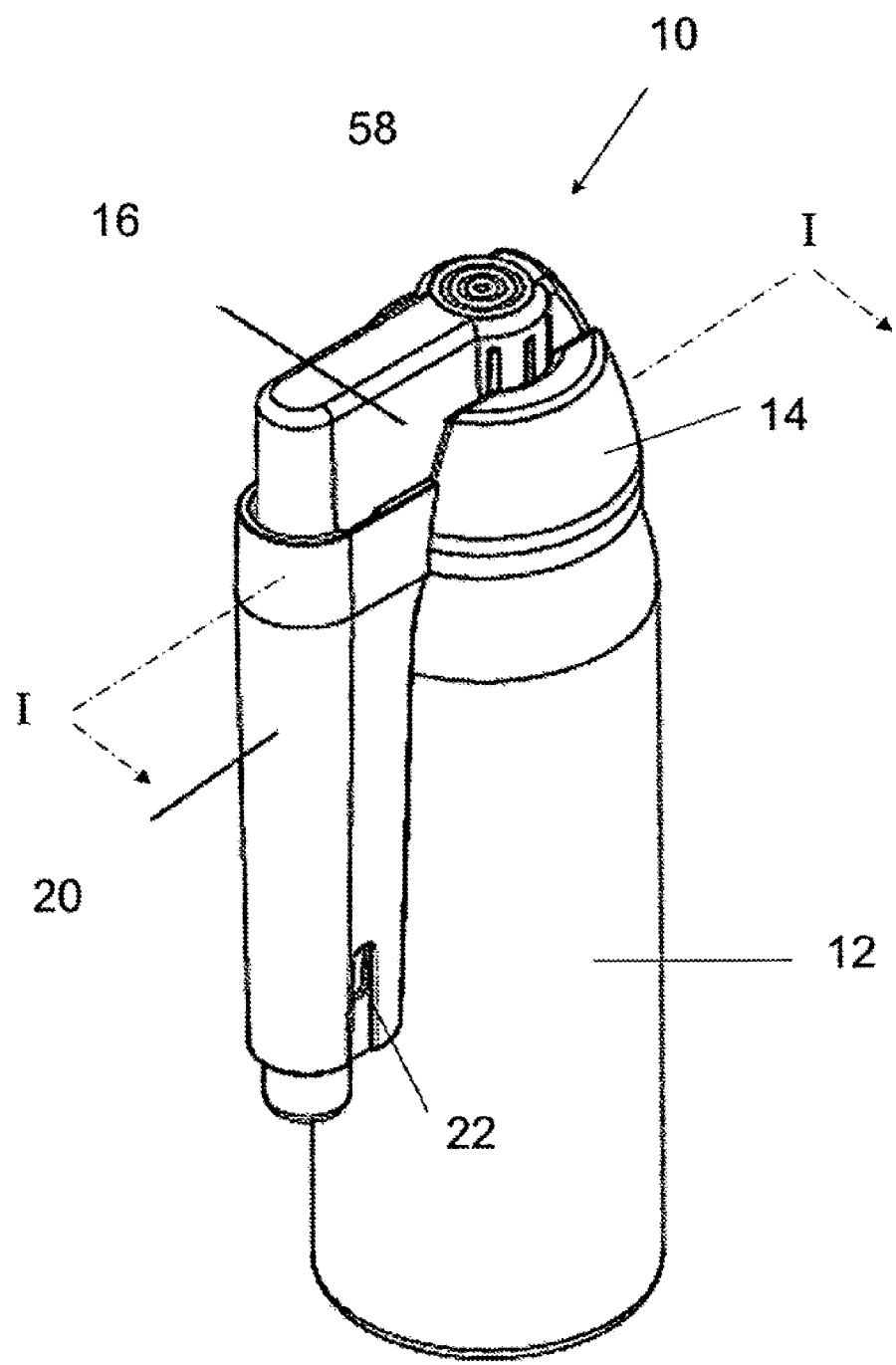
FIG. 1 is a perspective view of a first embodiment of the device of the present invention.
Figure 2:
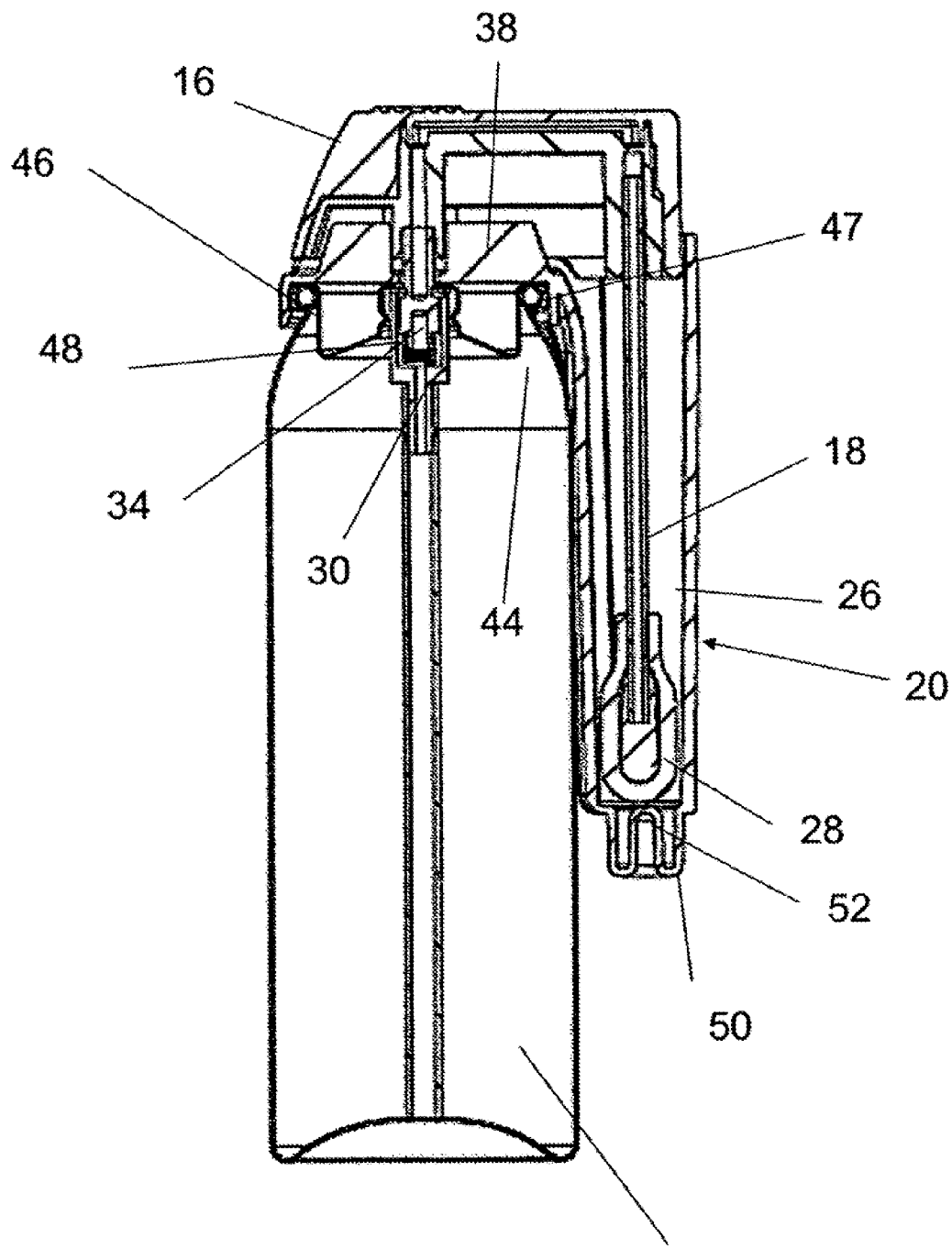
FIG. 2 is a cross-section of the device taken along line I-I of FIG. 1.

Referring to FIGS. 1 and 2, the cryogenic device 10 of the present invention includes a container 12 containing a pressurized liquid cryogen. A cap 14 is positioned at the top of container 12. Cap 14 includes a protective sheath 20 for encasing an applicator 18. An actuator assembly 16 is received within cap 14. Cap 14 and container 12 in combination with actuator assembly 16, applicator 18 and protective sheath 20 form the dispensing system of the present invention.

The device is adapted for use to remove various skin lesions, including verruca (warts), keratoses, achrocordon, molluscum contagiosum, age spots, dermatofibroma, keloids, granuloma annulare, porokeratosis plantaris, angiomas, lentigo maligna, keratoeanthoma, basal cell, Bowen's disease, lentigo discreta, chondrodermatitis, epithelial nevus, leokoplakia, granuloma pyogenicum, and Kaposi's sarcoma. However, for the sake of brevity, the following description will refer only to treatment of warts; treatments for the other conditions are similar, except that the sizes of the applicator tips and the duration of liquid refrigerant contact with the lesions can vary.

As shown in FIG. 2, the applicator tube 18 is secured to actuator assembly 16, which provides actuation to supply the refrigerant to applicator tube. It should be appreciated that applicator tube 18 can be removably or permanently attached to actuator assembly 16. Applicator tube 18 extends downwardly into sheath 20.

Applicator 18 is a hollow tube and includes a tip 28 made of a porous material disposed on and secured to one end thereof. Tip 28 can be made of any suitable porous material. such as but not limited to, cotton wool, open celled foams, a sintered thermoplastic, a sintered metal, a glass or ceramic frit, or a polyolefin or polyester non-woven fabric. U.S. Pat. No. 4,865,028 (Swart); U.S. Pat. No. 5,516,505 (McDow); U.S. Pat. No. 5,200,170 (McDow); U.S. Pat. No. 5,330,745 (McDow); U.S. Pat. No. 5,738,682 (Jensma); U.S. Pat. No. 6,296,410 (Ruizendaal); U.S. Pat. No. 6,092,527 (Jensma); U.S. Pat. No. 6,296,410 (Ruizendaal); U.S. Pat. No. 6,387,090 (Jensma); and U.S. Published Patent Application No. 2005/0043723 (Howlett et al.) disclose a variety of applicators and tip materials which may be used as the applicator tip in the present invention. The disclosure of these patents are incorporated herein by reference. Preferably, the applicator and tip is a foam over cotton tip such as disclosed in U.S. Pat. No. 5,738,682 (Jensma); U.S. Pat. No. 6,092,527 (Jensma); and U.S. Pat. No. 6,387,090 (Jensma). Preferably, tip 28 is secured to applicator tube 18, for example by thermal welding, ultrasonic welding, an adhesive, etc. as is known in the art.

When the valve of container 12 is opened, the liquid refrigerant fills applicator tube 18 and saturates tip 28. Then, tip 28 is briefly pressed against a wart or lesion to be removed from the skin. As refrigerant evaporates from the tip, it may be replenished during at least a portion of the treatment time by liquid remaining in the tube. Preferably, for hygienic reasons, the applicator tube 18 and tip 28 are used only once, and then discarded.

As shown in FIGS. 1-3E, in order to contain the refrigerant while the cryogen is being dispensed to saturate tip 28 of applicator 18, a protective sheath 20 is provided. Sheath 20 includes a vent 22 to allow excess gases to escape from the inside of the sheath. It should be appreciated that the vent can be an aperture disposed in the wall of the sheath or some other equivalent design. Moreover, the vent can be located at any point along the sheath.

Sheath 20 is connected to cap 14 and may be made of either clear or opaque molded material, such as polyethylene. Applicator tube 18 extends into protective sheath 20 and is contained completely therein upon assembly of the device. It should be appreciated that the diameter, length or width of sheath 20 can be varied to accommodate different sized and/or styled applicator tips and tube lengths. Applicator tube 18 can be either permanently or removably attached to actuator assembly 16. Sheath 20 acts as a protective shield to prevent cryogen from dripping onto the user during dispensing, and as an interlock to prevent dispensing unless the sheath is in place. As shown in the drawings, sheath 20 is placed completely about applicator 18 so that the user cannot come into contact with the liquid refrigerant either during or immediately after the initial dispensing. Sheath 20 includes a ridge 24 that extends from cap 14 to an interior passage 26 that receives applicator tube 18.

A waste reservoir 50 is located within a bottom end of sheath 20. Reservoir 50 acts to contain any excess cryogen that is not held within the porous material of tip 28. Reservoir 50 preferably has a shape that enables a visual indicator of whether enough cryogen has been dispensed. Having an inner stem 52 formed by the end decreases waste of cryogen because the filling area of the reservoir is limited. Sheath 20 can include an indicator mechanism for confirming that the porous material has been filled with cryogen. Reservoir 50 may also include an absorbent material that can fill with the excess cryogen. It should also be appreciated that different styled reservoirs are contemplated by the present invention. For example, the reservoir can be free of an inner stem or can have a shape that increases or decreases in diameter along its length.

In the embodiment of FIGS. 1-17, the sheath and cap are depicted as a single, unitary piece and can be comprised of a molded plastic resin, such as polypropylene, metal or other appropriate materials or combination of materials. Actuator assembly 16 can also be made from similar materials. It should be appreciated that other materials are contemplated by the present invention. Also, as illustrated by the other embodiments of the present invention, the sheath and cap can be separate removable pieces and need not be permanently attached.

Figure 3A:
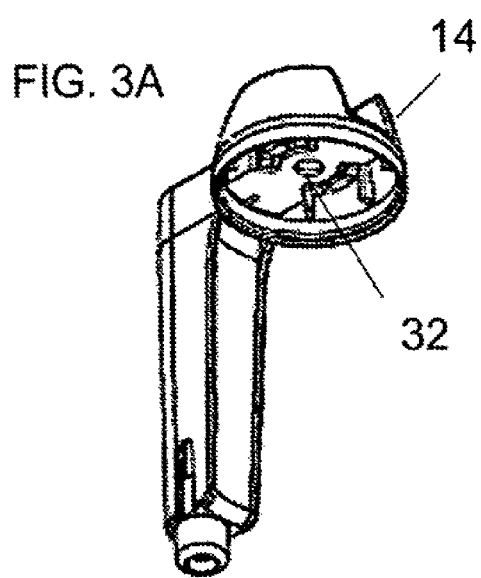
FIGS. 3A and 3B are perspective views of the cap and sheath of the device of the embodiment of FIG. 1.
Figure 3B:
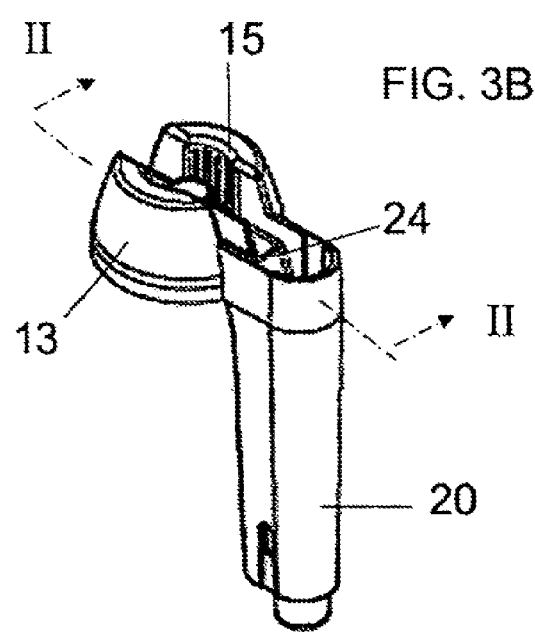
Figure 3D:
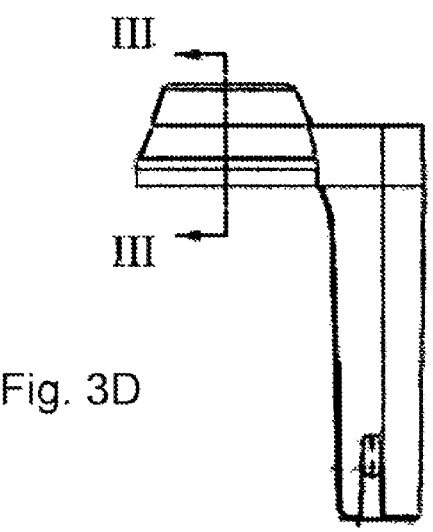
FIG. 3D is a side view of the cap and sheath of FIG. 3C.
Figure 3C:
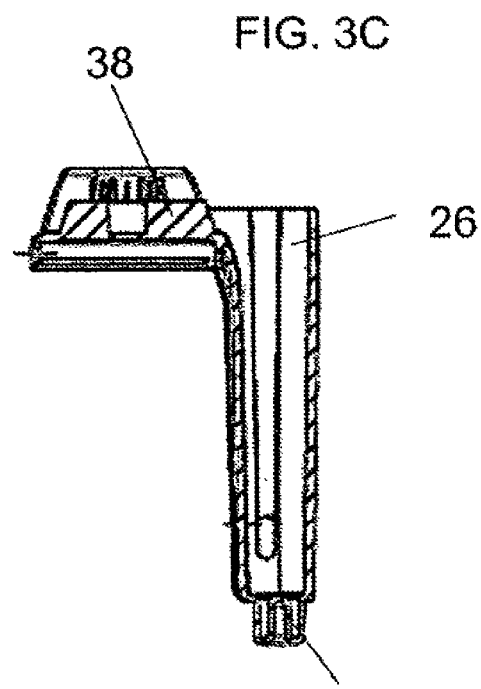
FIG. 3C is a cross-sectional view of the cap and sheath taken along line II-II of FIG. 3B.
Figure 3E:
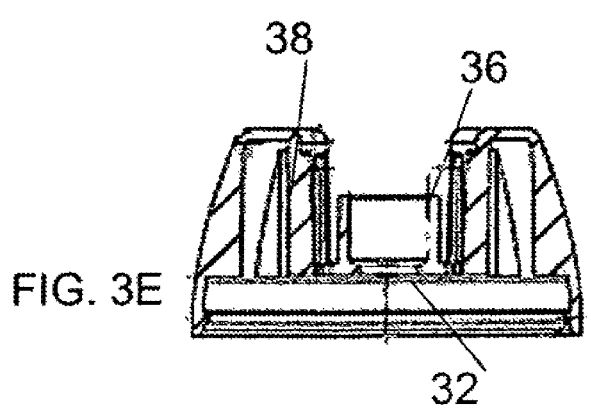
FIG. 3E is a cross-sectional view of the cap taken along line III-III of FIG. 3D.
Figure 6:
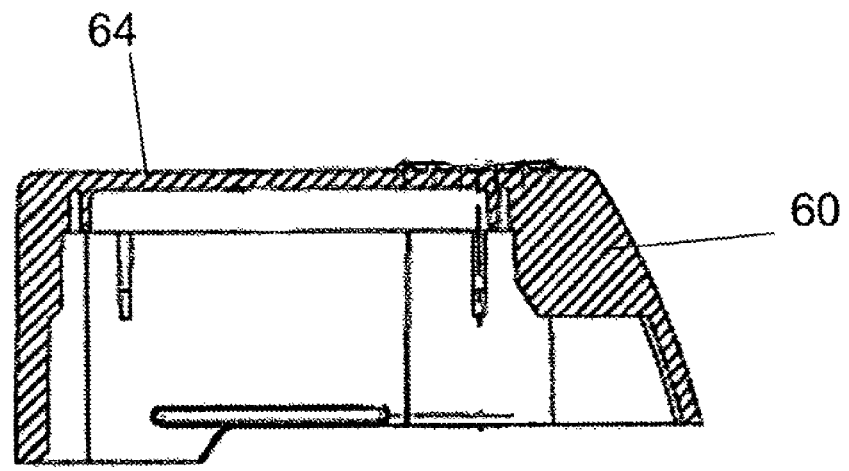
FIG. 6 is a cross-sectional view of the actuator shell taken along line V-V of FIG. 4C.

Referring again to FIG. 2, when cap 14 is attached to container 12, an outlet stem 34 of the container extends upwardly through cap 14. As also shown in FIG. 3E, cap 14 includes a boss 36 through which stem 34 extends. Stem 34 extends upwardly through an opening 32 (FIG. 3A) of cap 14 into boss 36. Boss 36 is encased by a circular rib 38 such that the top of boss 36 does not extend above rib 38. Rib 38 will be described further herein.

Aerosol container 12 contains the refrigerant and includes an annular side wall 42 and a top wall 44 that closes the upper end of annular side wall 42. A reduced diameter neck 46 is provided centrally in top wall 44 and extends upwardly therefrom. Neck 46 has a central opening 48 that is in fluid communication with the interior of container 12 for delivering a liquid refrigerant held therein. As is typical in the art, aerosol containers may be formed from plated steel, aluminum, and other materials; the choice of material is not particularly critical, resistance to corrosion from contact with the contents and an ability to withstand the internal pressures that are generated being the more important considerations.

The liquid refrigerant can be any suitable liquid refrigerant for use as a cryogenic agent to reduce the temperature of wart tissue to a temperature to freeze the skin, such that permanent, irreversible rupture of cellular membranes of cells of the skin lesion occurs while the cryogenic agent is evaporating. If the temperature of a wart is lowered below about $-20°$ C. for at least about twenty seconds, the wart tissue will be destroyed. Many low-boiling refrigerant/aerosol propellant materials are suitable for this purpose, including halogenated hydrocarbons, ethers, and hydrocarbons. For environmental reasons, the formerly very common chlorofluorocarbon refrigerants have been prohibited for most uses, generally being replaced by fluorohydrocarbon compounds; for example, the commercial refrigerant 1,1,1,2-tetrafluoroethane, which has a boiling point of $-26.5°$ C., is useful in the present invention. The materials may be mixtures of refrigerant compounds to lower the container internal pressures, to achieve a desired boiling point, or for other reasons. Those skilled in the art are aware of numerous useful refrigerant compounds and mixtures.

Examples of useful mixtures are: 82 weight percent dimethyl ether and 18 weight percent propane; and 95 weight percent dimethyl ether, 2 weight percent propane, and 3 weight percent isobutane. For purposes of the present invention, a very suitable liquid refrigerant is a mixture of 75 weight percent dimethyl ether and 25 weight percent propane, which produces temperatures below about $-20°$ C. on the surface of skin of a person when applied.

A conventional spring-loaded pressurized aerosol valve (not shown) is provided in neck 46 of container 12. The construction details of the valve are well known and the specific construction of the valve does not form part of the present invention. Examples of such valves can be found throughout the patent literature, for example, in U.S. Pat. Nos. 6,039,306; 6,318,603; and many other patents; as well as in A. R. Gennaro, Ed, *Remington: The Science and Practice of Pharmacy,* 20$^{th}$ Ed., Lippincott, Williams & Wilkins, Baltimore, Md., 2000, pages 971-972; the entire disclosures of which are incorporated herein by reference.

Top wall 44 of cap 14 engages an annular rim 47 of container 12 to secure the cap thereon. A dip tube 30 is connected with the valve and extends into container 12, and outlet stem 34 extends out of container 12. It will be appreciated that dip tube 30 can be made to extend into the interior of container 12 for only a very short distance, or can even be eliminated, so that liquid refrigerant can be delivered even if container 12 is inverted. As is well known in the art, when outlet stem 34 is depressed, the valve is opened, and the refrigerant will exit container 12 through dip tube 32, the valve and outlet stem 34, until the outlet stem 34 is returned to its normal position (typically from pressure exerted by a spring disposed within the valve) and the valve is closed.

Referring to FIGS. 3A-3E, cap 14 includes side walls 13, 15. As shown in FIG. 1, when the components are assembled for dispensing, actuator assembly 16 is positioned between sides 13, 15 of cap 14. The spacing between side walls 13 and 15 should be minimal, for example, less than ½ inch.

As shown in more detail in FIGS. 4A-5C, actuator assembly 16 is formed of an actuator shell 60 and an actuator insert 62. Actuator shell 60 has a top 64 that includes a scored cue 58 for the user's finger. Actuator insert 62 is completely received within shell 60 and includes an upper portion 66 extending from a base portion 68. Referring to FIGS. 4B, 5C, 6 and 7, top 66 of insert 62 includes a slot 72. When the insert is positioned within the shell, slot 72 forms a passage between top portion 64 and top 66 (FIG. 5C).

Figure 7:
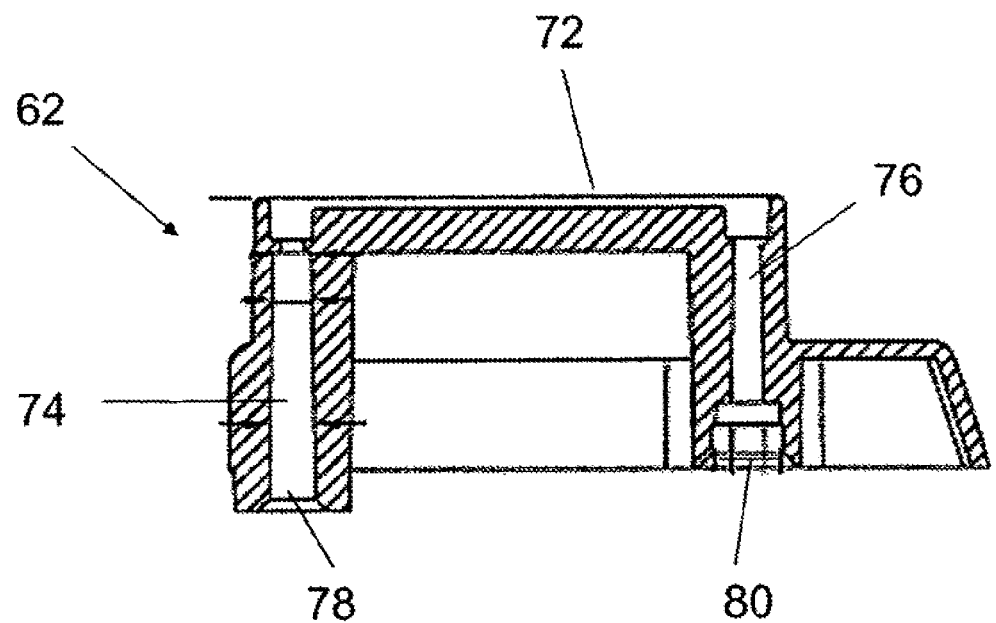
FIG. 7 is a cross-sectional view of the actuator insert taken along line VI-VI of FIG. 4D.

As shown in FIG. 7, insert 62 also has two inner passages 74, 76 that communicate with passage/slot 72 to form a passageway 70, illustrated here as a u-shaped passageway, extending therethrough when the shell and insert are assembled. Passageway 70 has opposed ends 78 and 80. One end 78 receives the applicator tube 18 (FIG. 2). The other end 80 of passageway 70 receives outlet stem 34 such that outlet stem 34 is coaxial and in fluid communication with passageway 70. End 80 has a shoulder 82 in surrounding relation to the opening of passageway 70. Actuator assembly 16 sits in cap 14 such outlet stem 34 is received in the passageway at end 80 with the upper edge of outlet stem 34 abutting against inner annular shoulder 82.

Optional cue 58 guides the user to position the fingertip for maximum actuation. As a result of pressure applied to upper surface of actuator 16 at cue 58, the actuator assembly 16 pivots about ridge 24 and inner annular shoulder 82 of insert 62 forces outlet stem 34 inwardly towards container 12 in order to open the valve and release the refrigerant, which then travels from outlet stem 34, through passageway 70.

Boss 26 of cap 14 will prevent dispensing of cryogen if actuator assembly 16 is not positioned correctly on cap 14. Further, as shown in FIG. 2, outlet stem 34 cannot be positioned within end 78 of passageway 40 due to dimensioning. Not only could a user not position actuator 16 on cap 14 in this manner, the end of applicator tube 18 could not be secured in end 80 of passageway 70. As shown in detail in FIG. 5C, at end 78 the outer diameter of applicator tube 18 is smaller than the inner diameter of end 80 of passageway 70. Thus, the fit will be too loose and the applicator tube 18 will fall out. Moreover, due to the narrow spacing between sidewall 13, 15 of cap 14, and because the top of boss 36 is recessed in rib 38, a user could not gain access to outlet stem 34 to actuate the valve.

Figure 8:
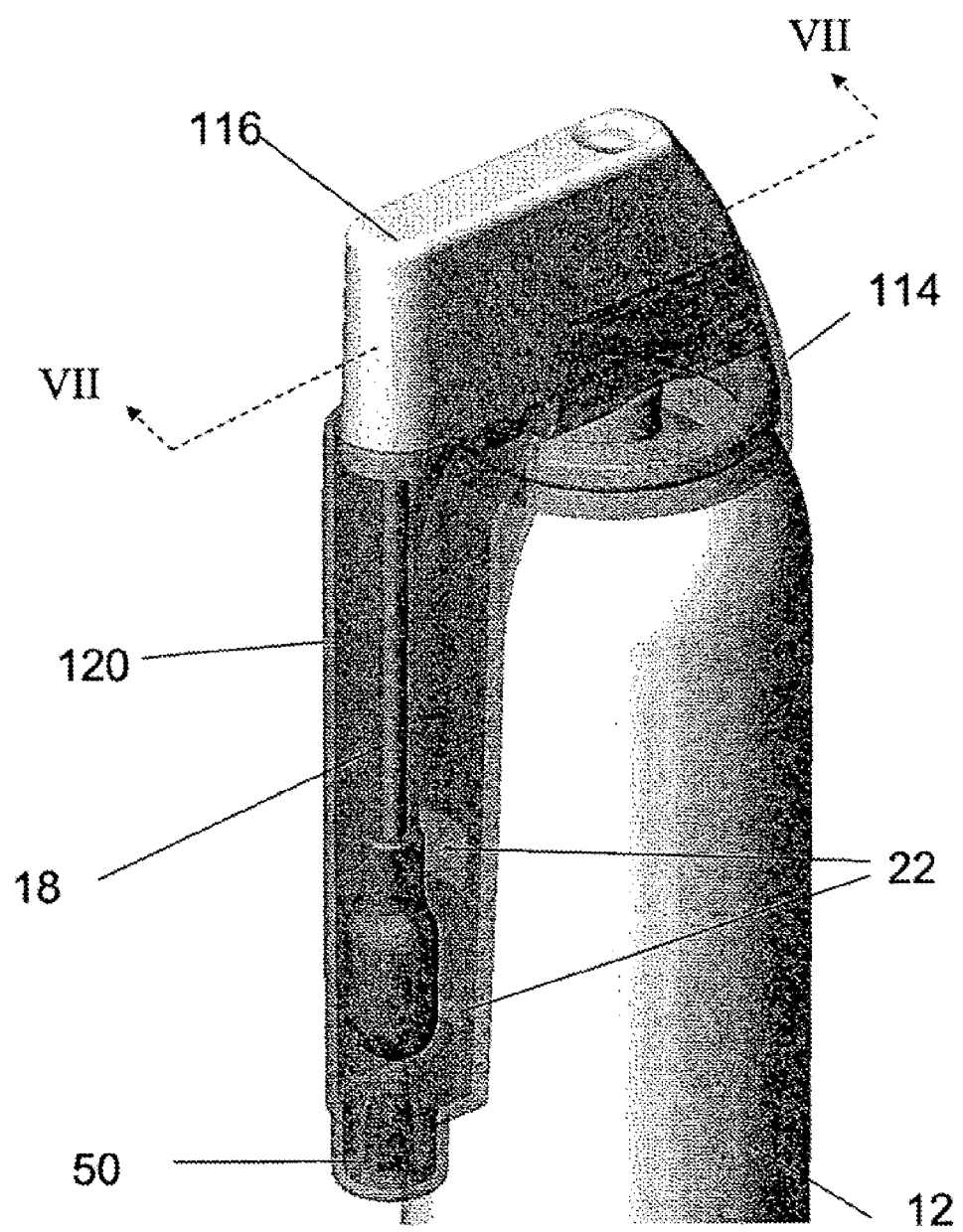
FIG. 8 is a partial cross-sectional view of another embodiment of the device of the present invention.
Figure 9:
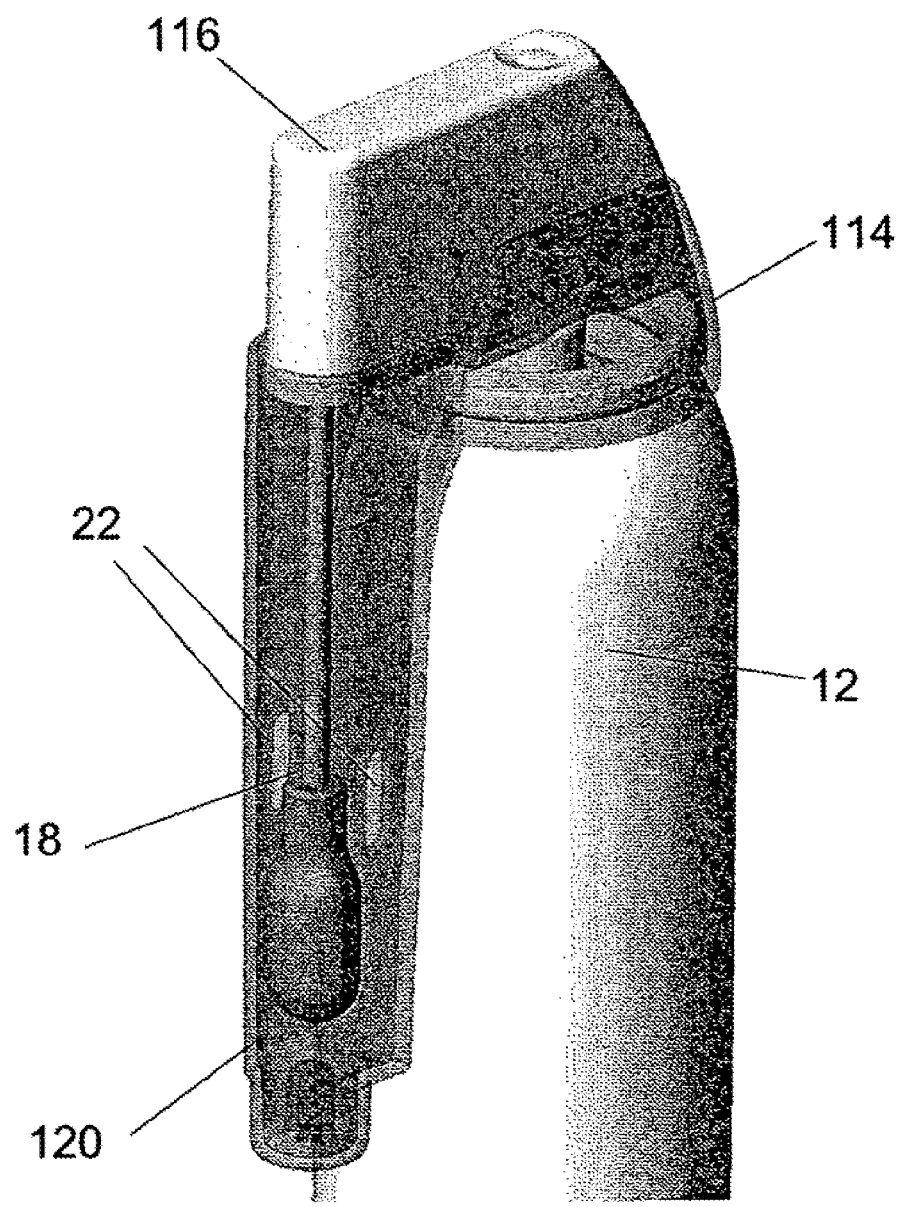
FIG. 9 is a partial cross-sectional view of the device of FIG. 8 having an alternate vent design.

Another embodiment of a device according to the invention is shown in FIGS. 8-15. Device 100 includes applicator tube 18 (with a porous tip as discussed above) secured to an actuator 116, which provides actuation to supply the refrigerant to applicator tube. It should be appreciated that applicator tube 18 can be removably or permanently attached to actuator 116. Applicator tube 18 extends downwardly into sheath 120. Protective sheath 120 includes vents 22 positioned in the wall thereof. FIG. 9 illustrates an alternate position for the vents. In this embodiment, vents 22 are positioned in the sides of the sheath.

Figure 10:
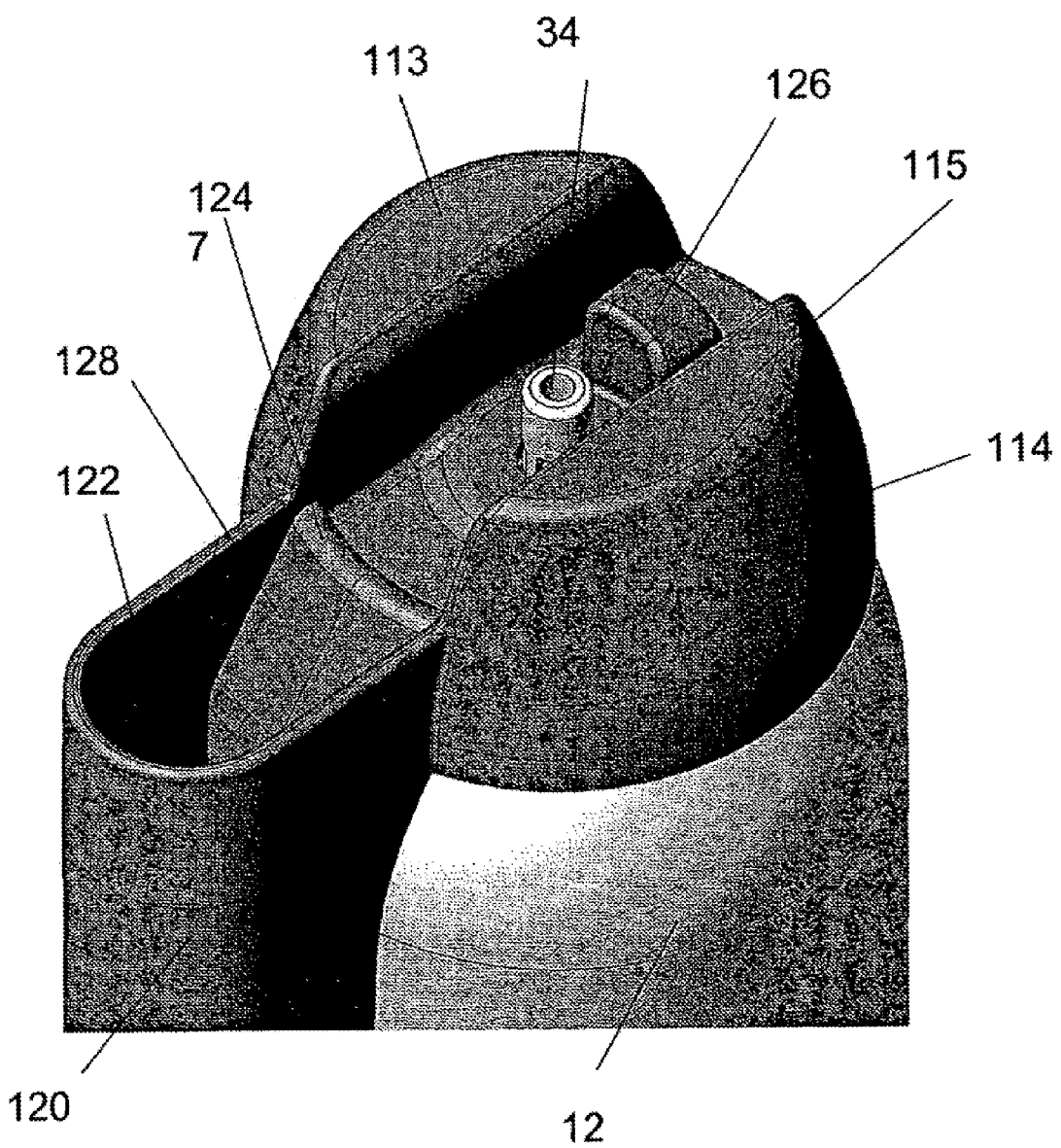
FIG. 10 is a perspective view of the cap of the device of FIG. 8.

Referring to FIG. 10, cap 114 includes side walls 113, 115. As shown in FIG. 8, when the components are assembled for dispensing, actuator 116 is positioned between sides 113, 115 of cap 114. The spacing between side walls 113 and 115 should be minimal, for example, less than ½ inch. When cap 114 is attached to container 12, an outlet stem 34 of the container extends upwardly through cap 114. Positioned alongside outlet stem is a safety lockout boss 126, which will be described further herein. Sheath 120 is formed integral with cap 114 and includes a ramp 128 that extends from cap 114 to an interior passage 122 that receives applicator tube 18. Cap 114 also includes a pivot ridge 124 for actuator 16, which will also be described further herein.

Figure 11:
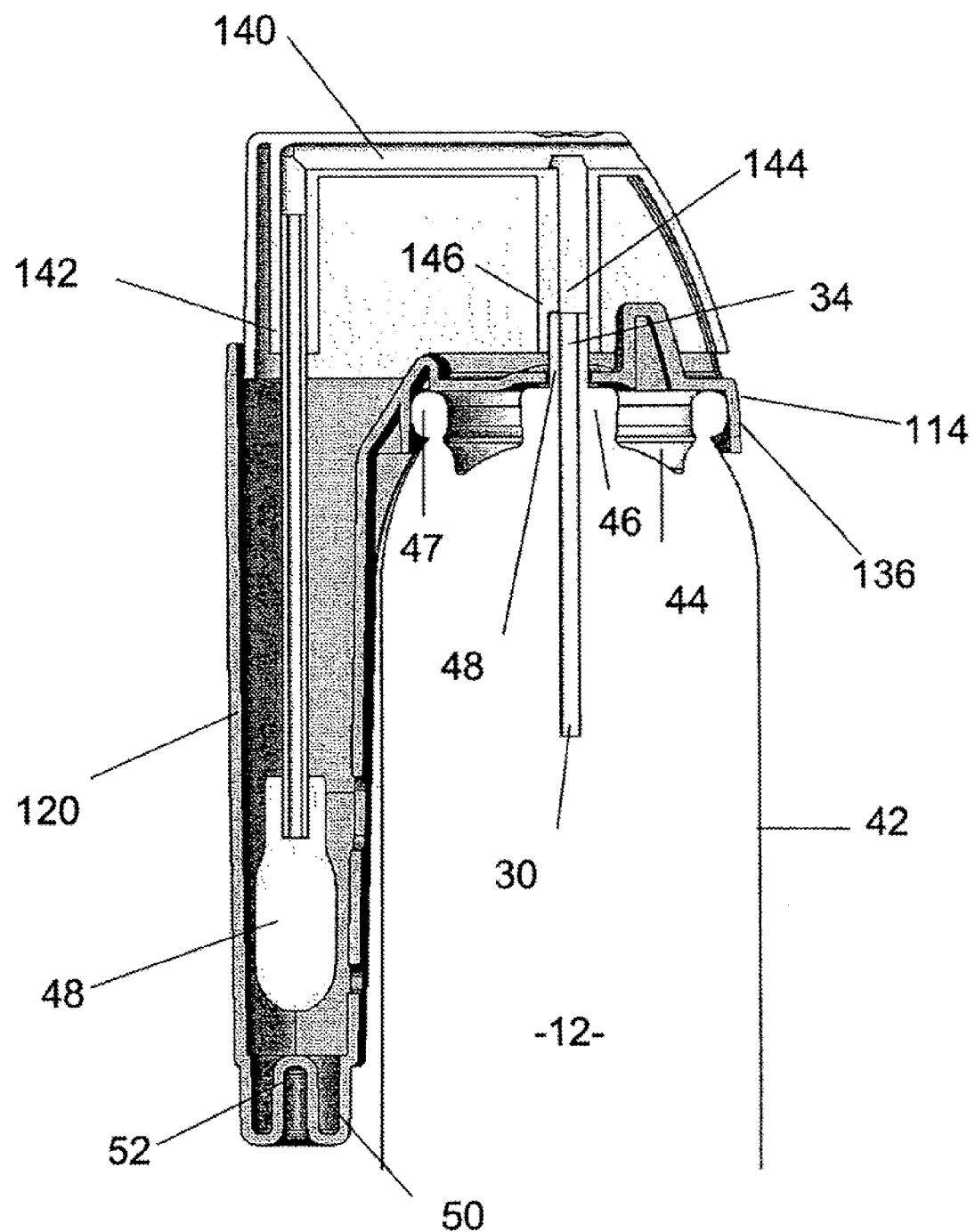
FIG. 11 is a cross-sectional view of the dispensing system taken along line VII-VII of FIG. 8.
Figure 12:
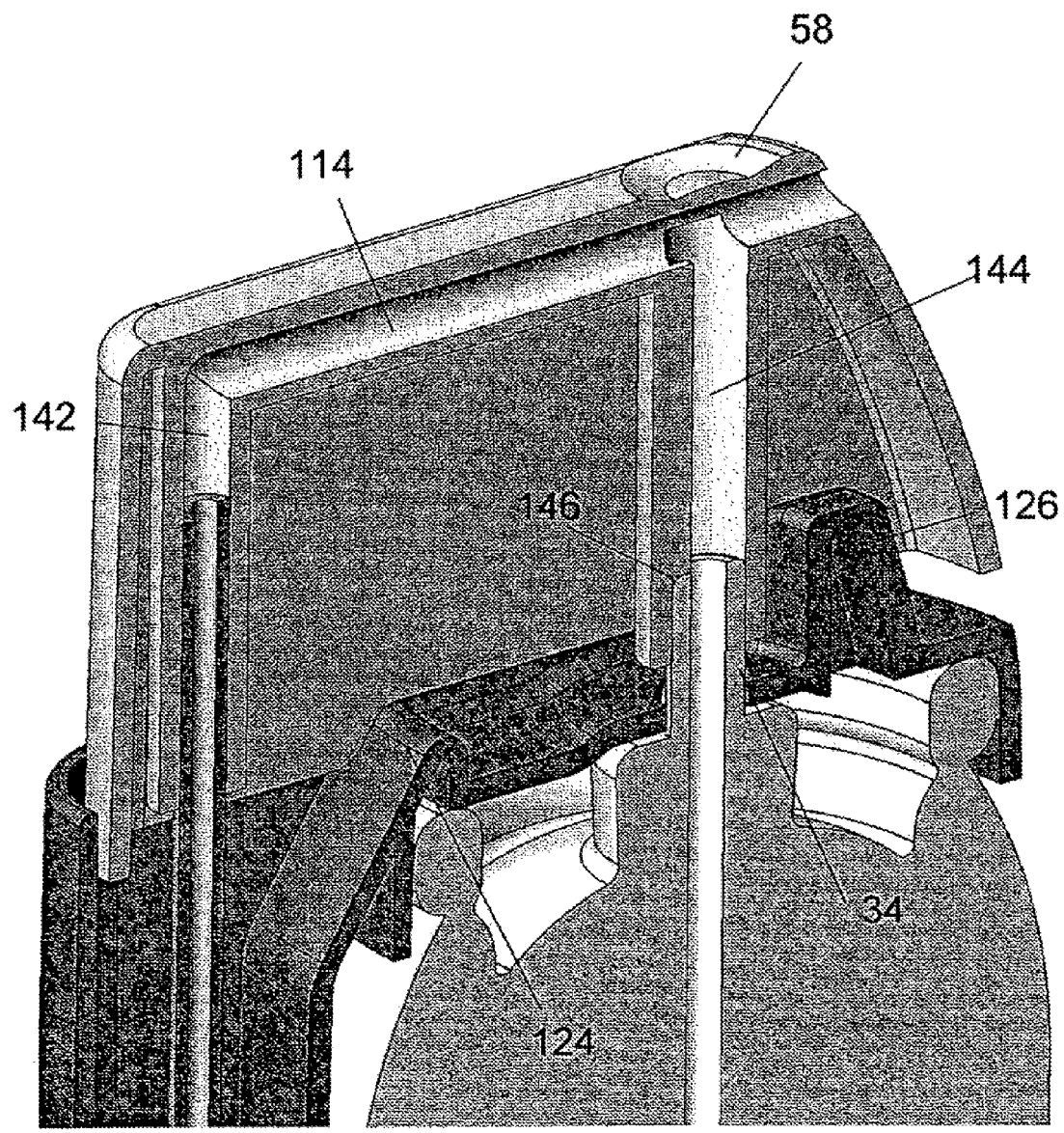
FIG. 12 is an enlarged cross-sectional view of the actuator and cap assembly of FIG. 11.

As shown in more detail in FIGS. 11 and 12, actuator 116 includes a u-shaped passageway 140 extending therethrough. Passageway 140 has opposed ends; one end 142 receives the applicator tube 18. The other end 144 of passageway 140 receives outlet stem 34 such that outlet stem 34 is coaxial and in fluid communication with passageway 140. End 144 has a shoulder 146 in surrounding relation to the opening of passageway 40. Actuator 116 sits in cap 114 such outlet stem 34 is received in the passageway with the upper edge of outlet stem 34 abutting against inner annular shoulder 146.

The top of the actuator can include cue 58 to guide the user to position the fingertip for maximum actuation. As a result of pressure applied to upper surface of actuator 116 at cue 58, the actuator 116 pivots about ridge 124 and inner annular shoulder 146 forces outlet stem 34 inwardly towards container 12 in order to open the valve and release the refrigerant, which then travels from outlet stem 34, through passageway 140.

Figure 13:
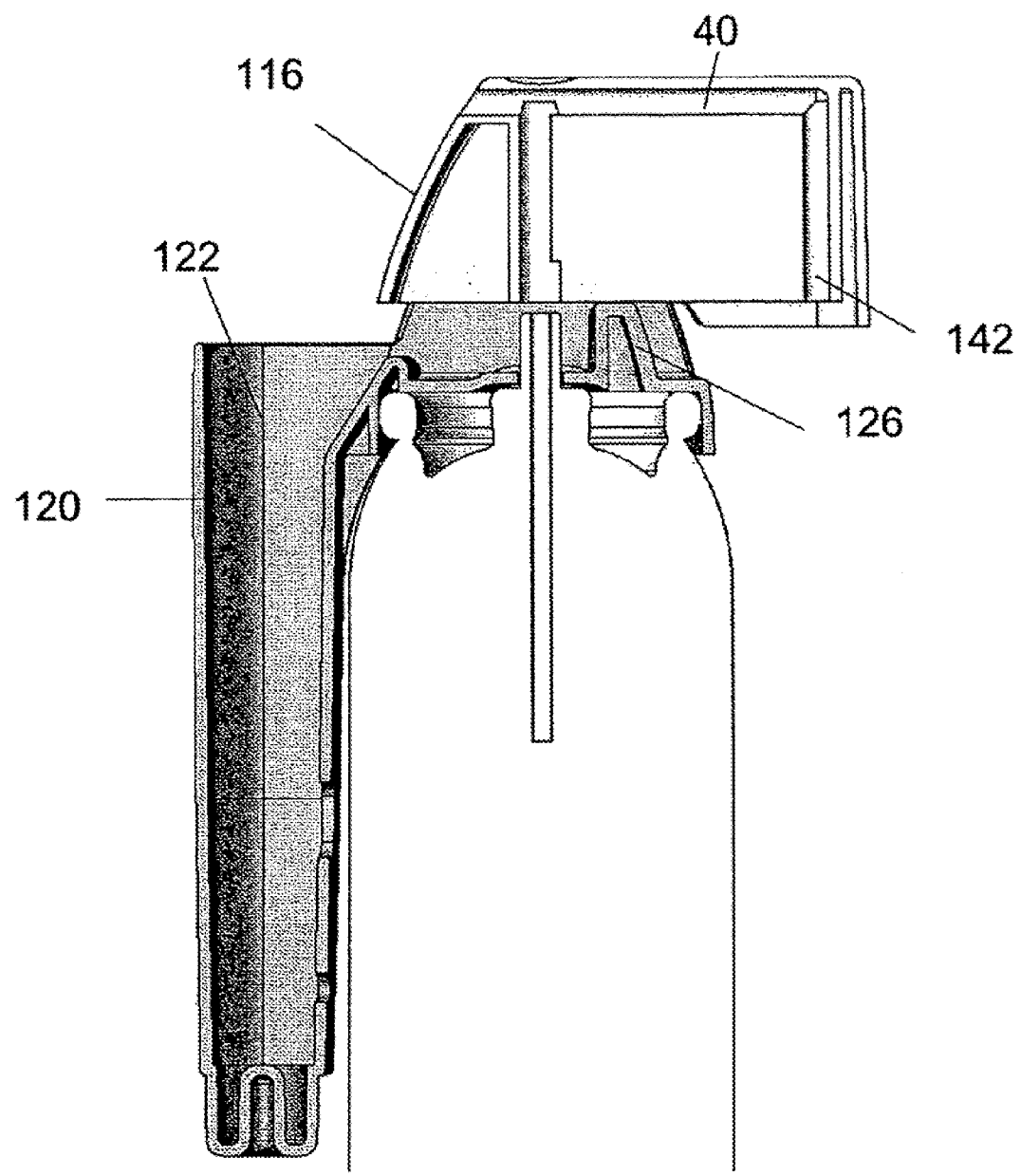
FIGS. 13 and 14 are cross-sectional views of the second embodiment of the present invention illustrating the inability to incorrectly position the actuator on the cap.
Figure 14:
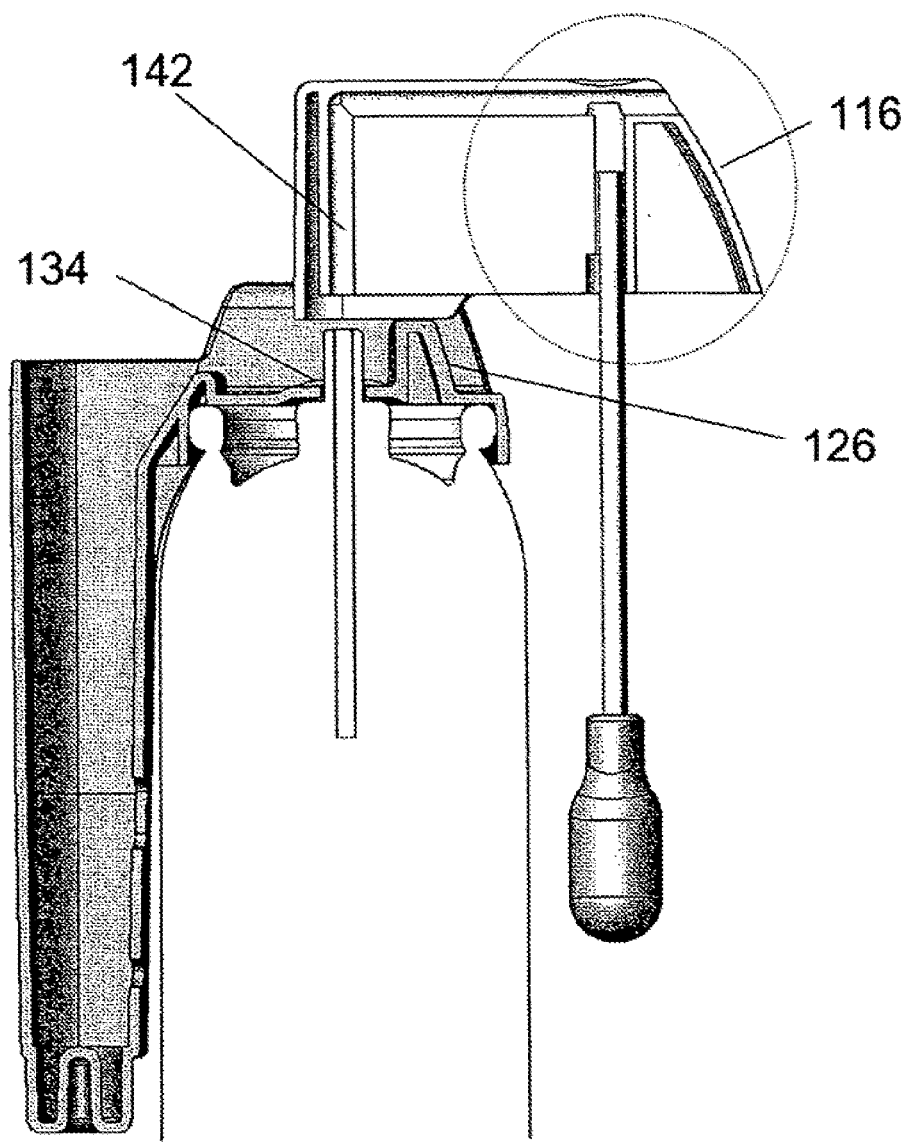
Figure 15:
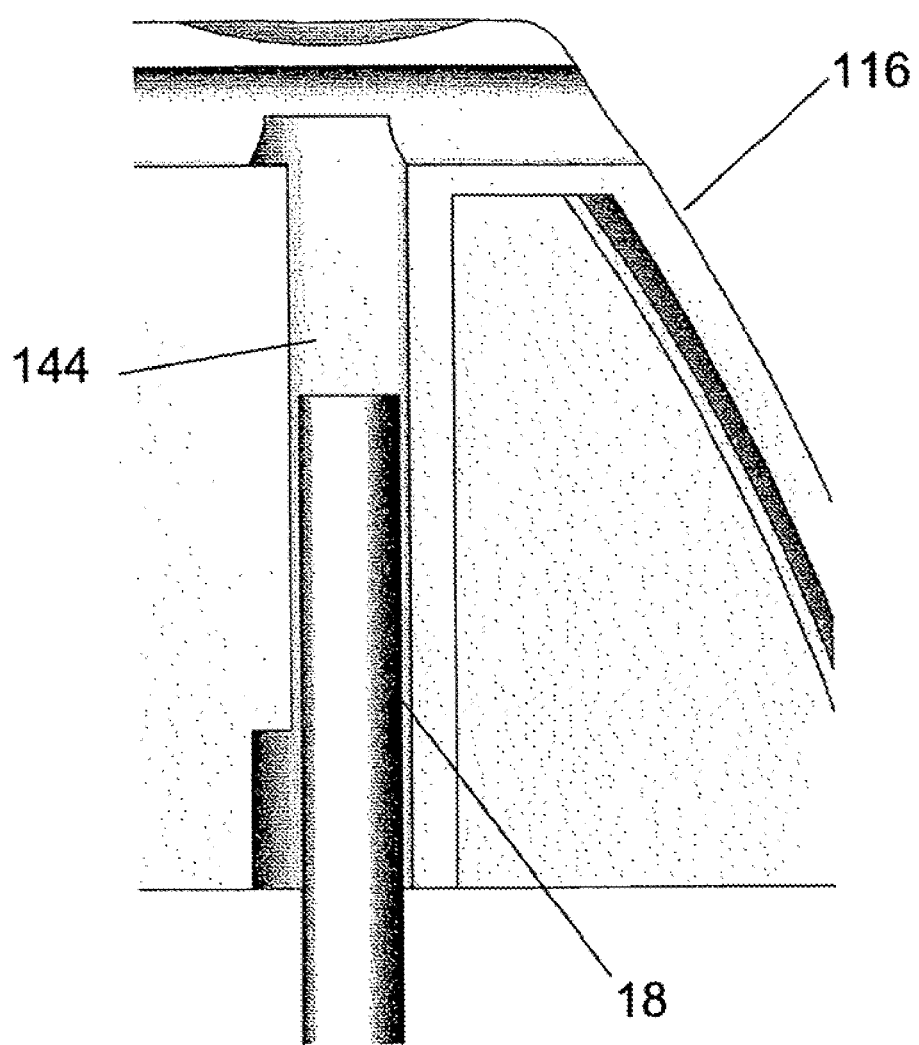
FIG. 15 is an enlarged cross-sectional view of the indicated portion of FIG. 14.

Referring to FIGS. 13-15, boss 126 of cap 114 will prevent dispensing of cryogen if actuator 116 is positioned incorrectly on cap 114. As shown in FIG. 13, boss 126 prevents actuator 116 from being positioned backwards, i.e., wherein end 142 of passageway 140 is not in communication with passage 122 of sheath 120. Further, as shown in FIG. 14, outlet stem 34 cannot be positioned within end 142 of passageway 140 due to dimensioning and the interference between boss 126 and rib of actuator 116. Not only could a user not position actuator 116 on cap 114 in this manner, the end of applicator tube 18 could not be secured in end 144 of passageway 140. As shown in detail in FIG. 15, at end 144 the outer diameter of applicator tube 18 is smaller than the inner diameter of passageway 140. Thus, the fit will be too loose and the wand will fall out.

Figure 16:
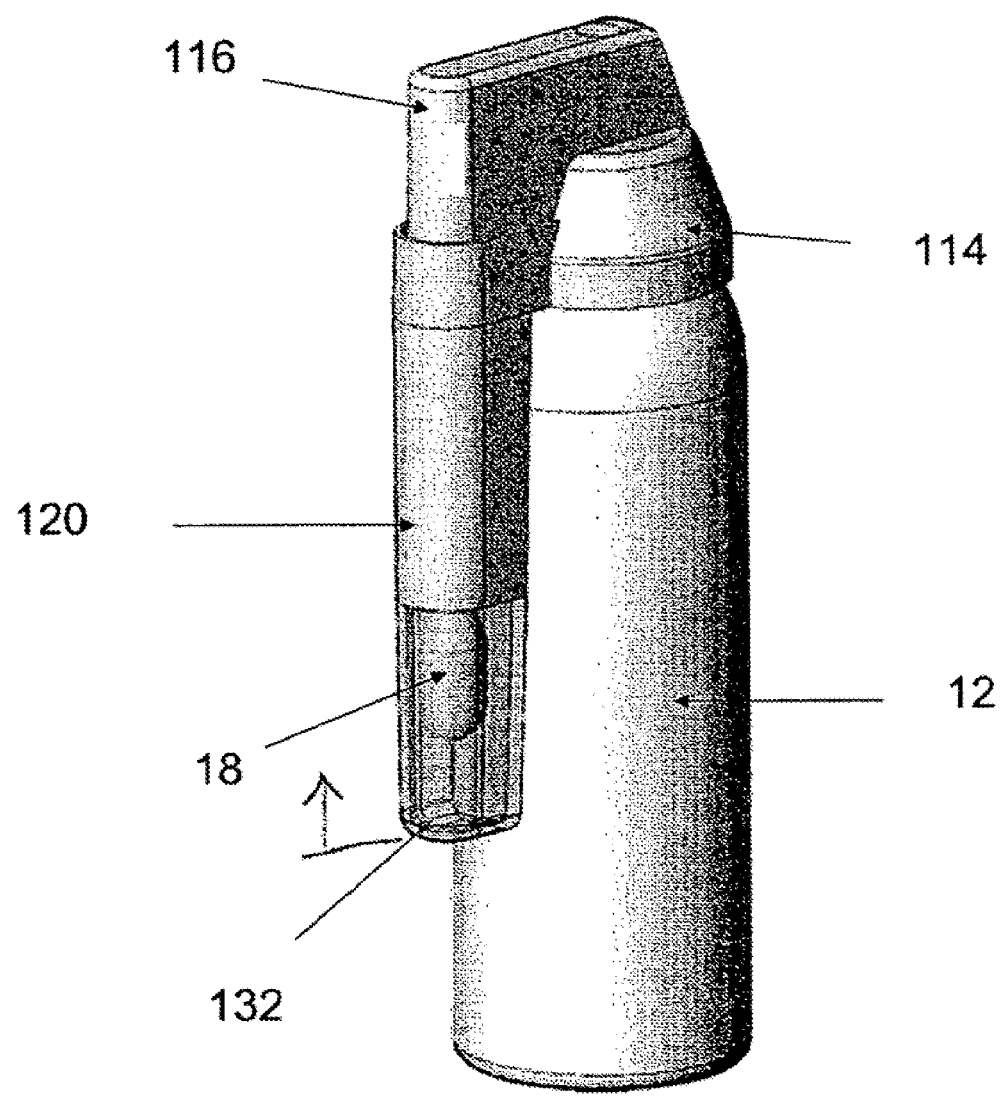
FIG. 16 is a perspective view of another embodiment of the device of the present invention.
Figure 17:
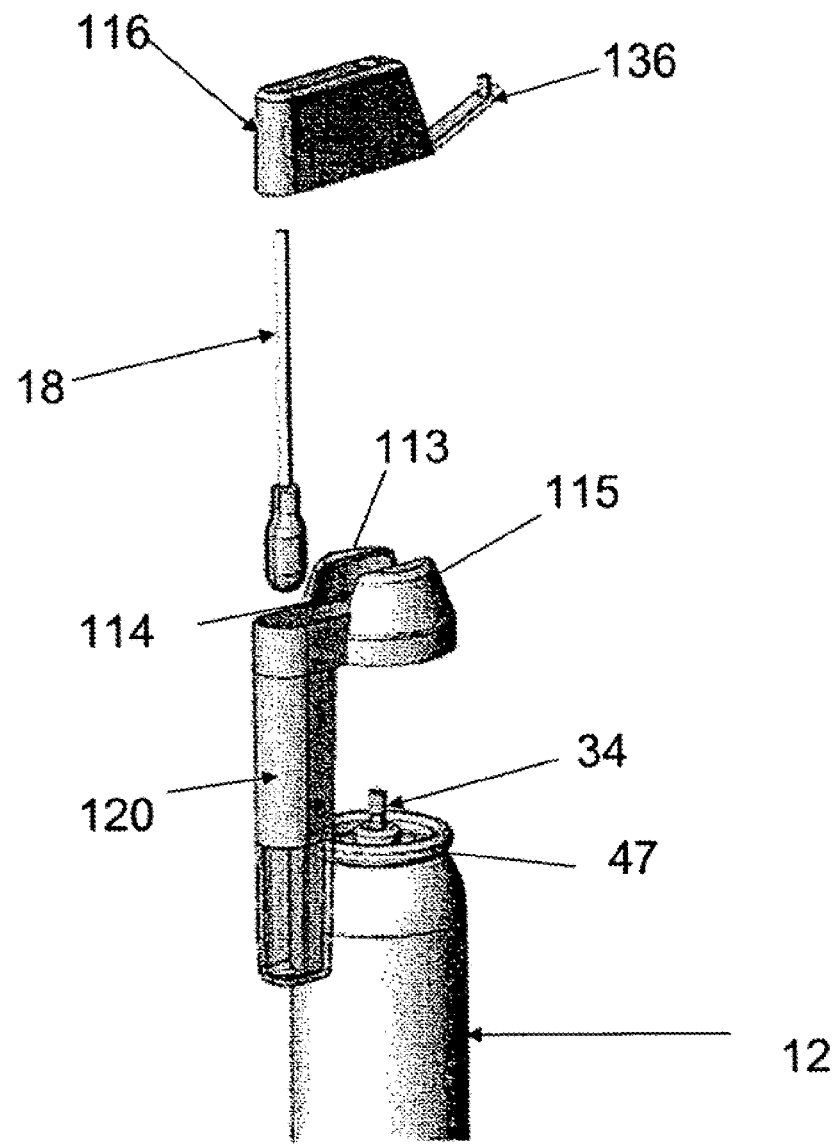
FIG. 17 is a perspective view of the device of FIG. 16 unassembled.

Referring to FIGS. 16 and 17, in another embodiment of the present invention, where like elements have been referred to with the same numeral as the previous embodiment, sheath 120 can include a transparent lower portion 132. Actuator 116 can include a hinged end 136.

Figure 18:
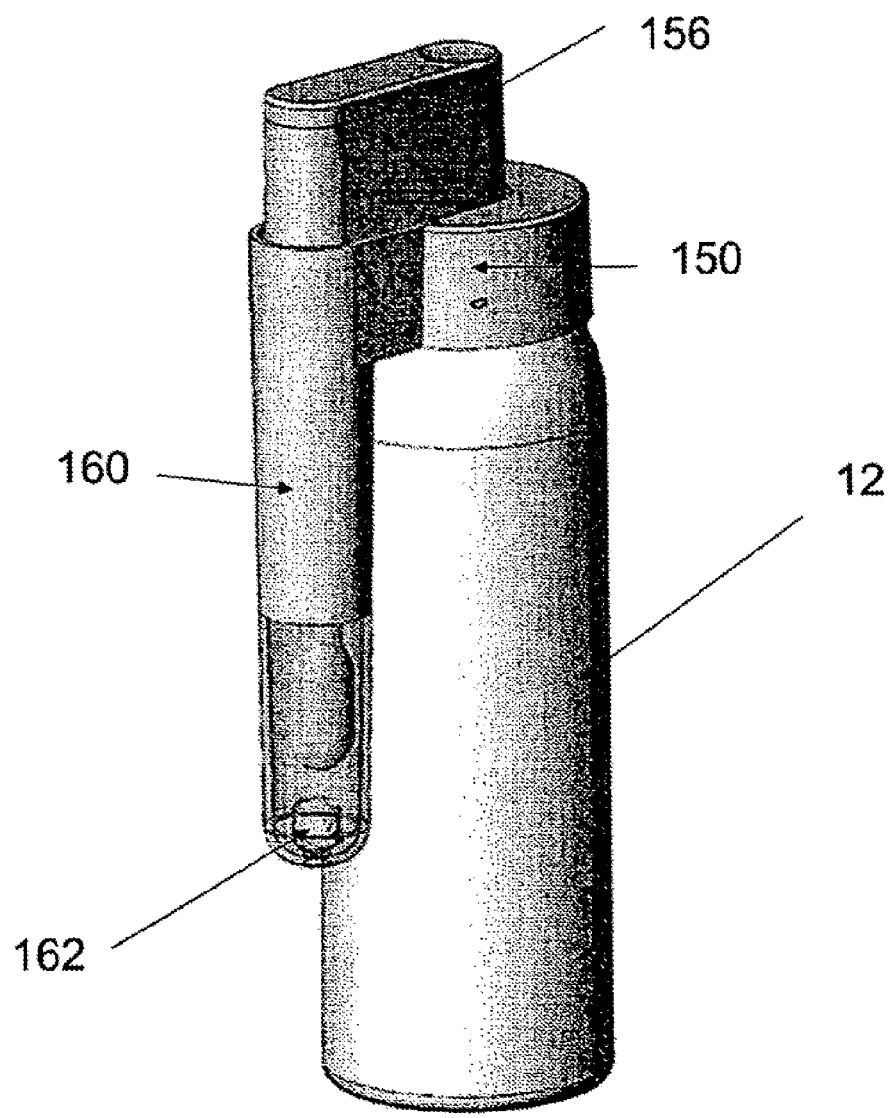
FIG. 18 is a perspective view of still another embodiment of the device according to the present invention.
Figure 19:
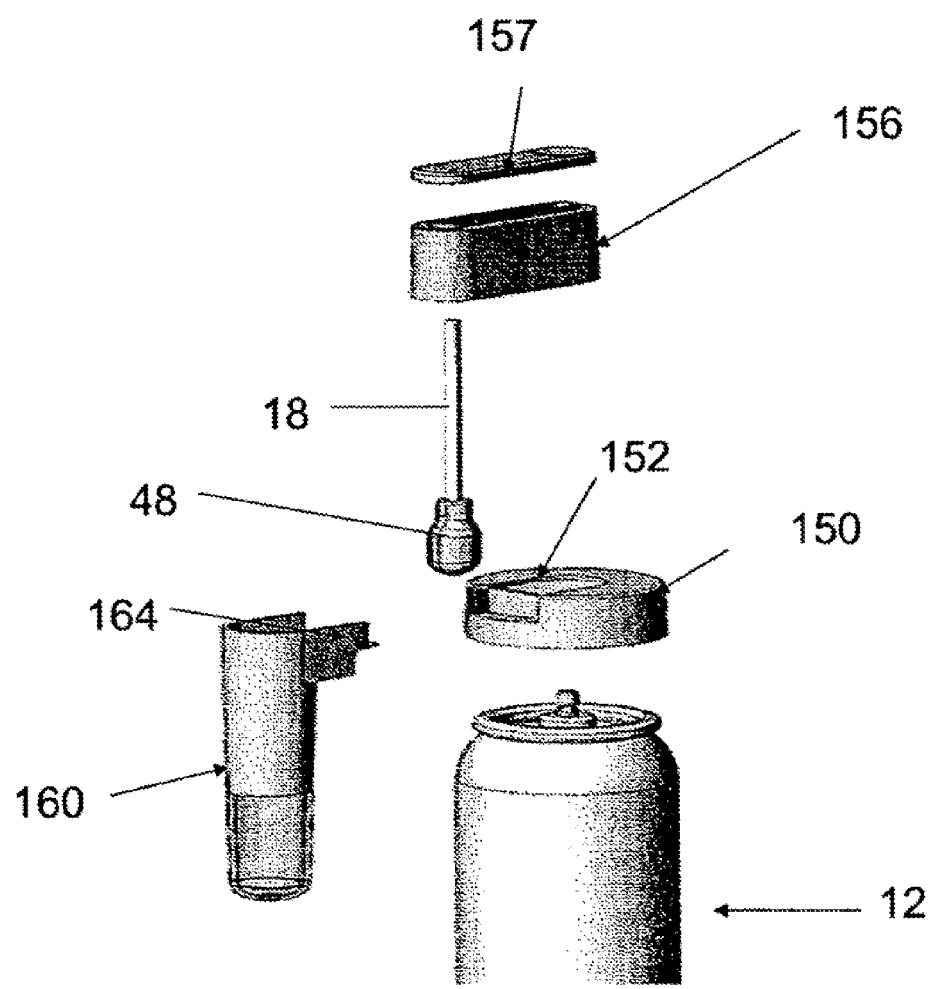
FIG. 19 is a perspective view of the device of FIG. 18 unassembled.

Referring to FIGS. 18 and 19, in another embodiment of the present invention, cap 150 and sheath 160 are formed of two separate interlocking pieces. Cap 150 includes an aperture 152 for receiving an actuator 156. Actuator 156 includes a top section 158, and an inner passageway which communicates with applicator 16 and outlet stem 34, as in the previous embodiment. Sheath 160 can also include a reservoir 162 and indicia for indicating delivery of cryogen to tip 48. Sheath 160 includes arms 164 which extend on each side of actuator to interlock the sheath to the actuator and cap. Bud 48 can have a shorter length, for example, from the top of the bud to the bottom of the tube, the length of the bud could be of and about 40-80 mm.

Figure 20:
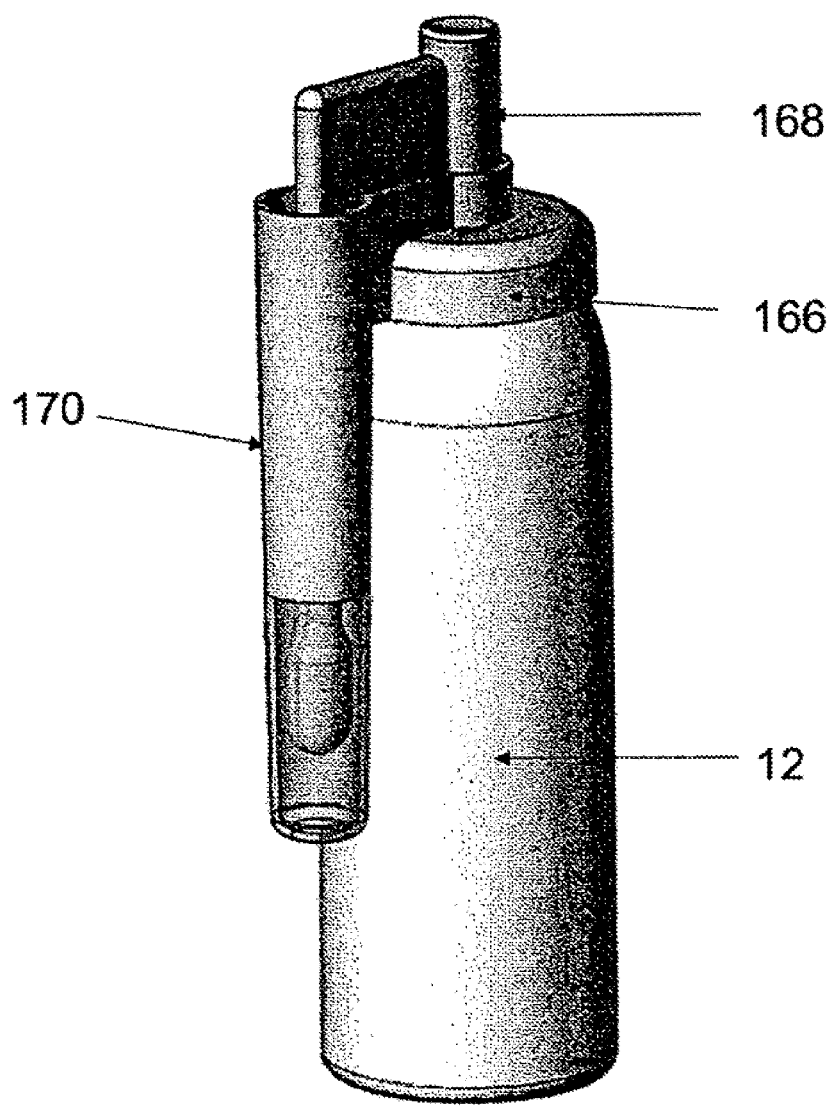
FIG. 20 is a perspective view of yet another embodiment of the device according to the present invention.
Figure 21:
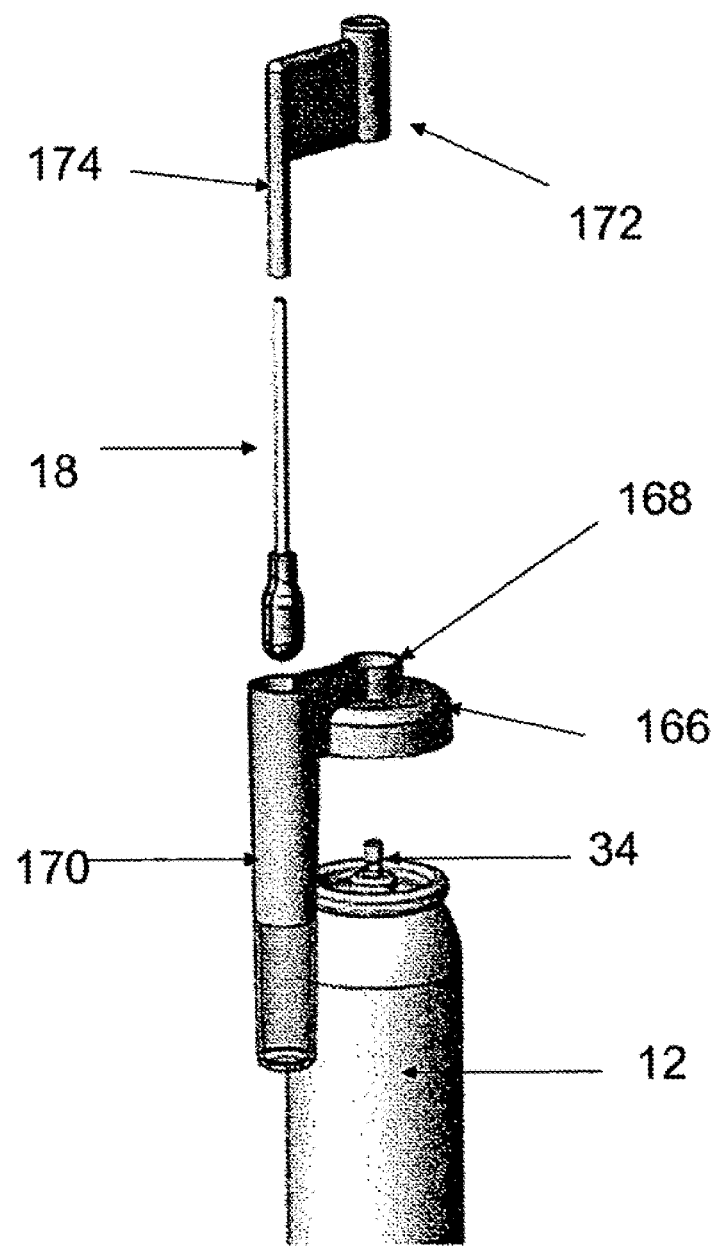
FIG. 21 is a perspective view of the unassembled device of FIG. 20.

In the embodiment of FIGS. 20 and 21, a cap 166 and sheath 170 are formed of a single, unitary piece. Cap 166 includes a slot 168 for receiving an actuator 172. As with the other embodiments of the present invention, actuator 172 includes an internal passageway that communicates with the outlet stem 34 and applicator 18. Applicator 18 is positionable within a tube 174 of actuator 172. Dispensing of the cryogen cannot occur unless cap 166/sheath 170 and actuator 172 are assembled on container 12.

Figure 22:
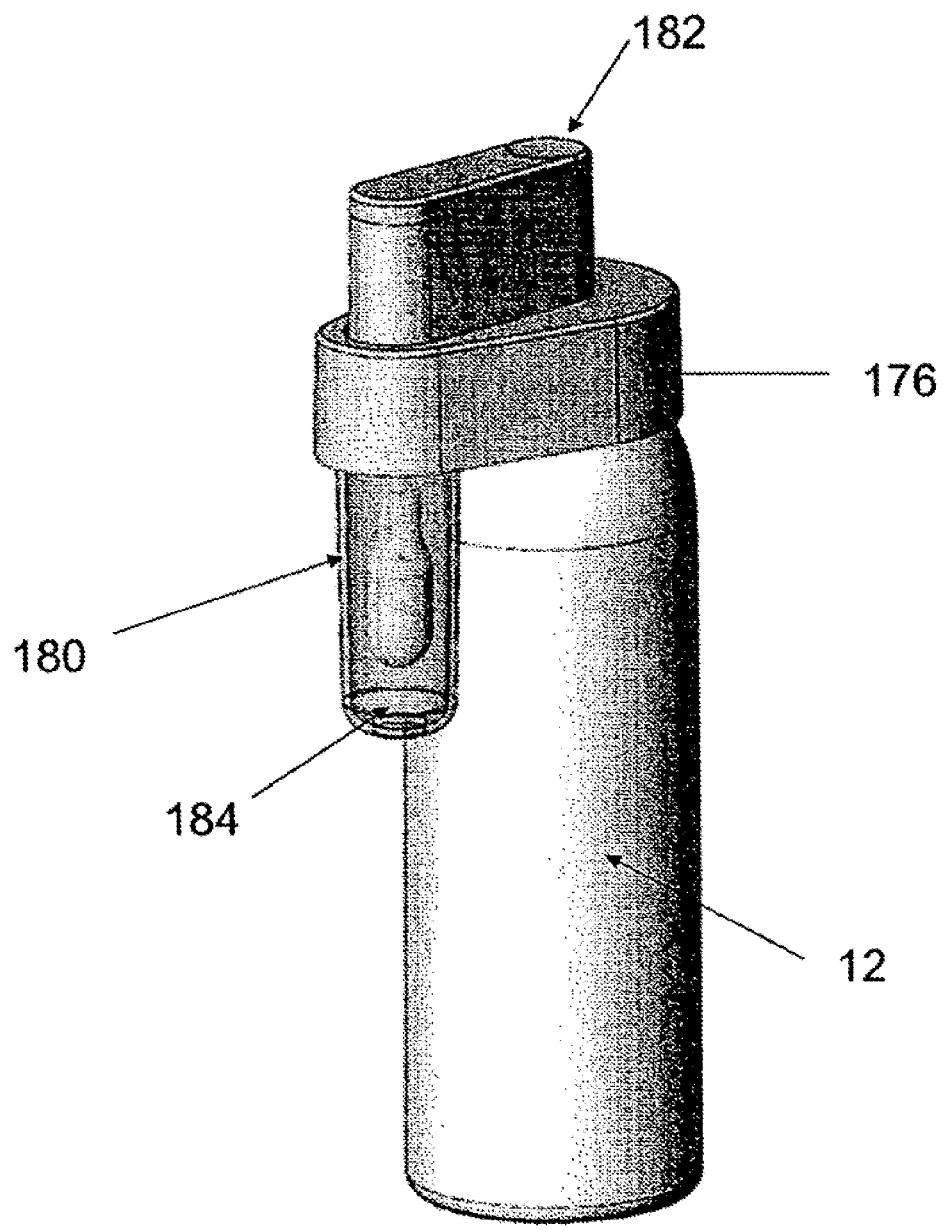
FIG. 22 is a perspective view of another embodiment of the device according to the present invention.
Figure 23:
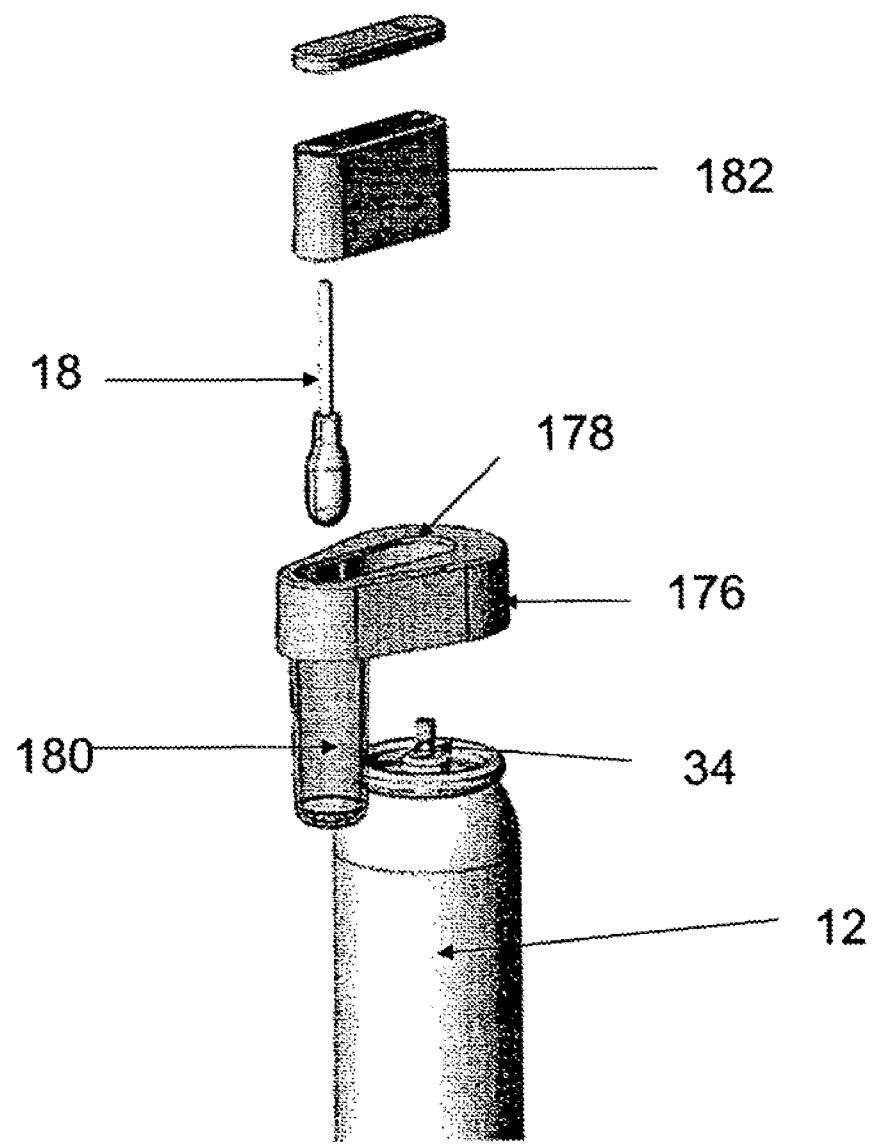
FIG. 23 is a perspective view of the device of FIG. 22 unassembled.

Referring to the embodiment FIGS. 22 and 23, a cap 176 and sheath 180 may be formed of a single, unitary piece. In this embodiment, cap 176 includes an elongated slot 178 through which applicator 18 and actuator 182 are positioned. When assembled, outlet stem 34 extends through slot 178 to communicate with actuator 182 and the passageway therein. Sheath 180 also includes a reservoir 184 for containing the waste cryogen.

Figure 24A:
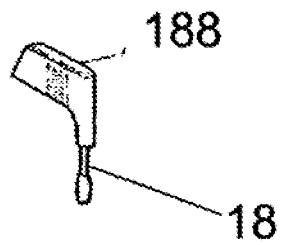
FIGS. 24A and 24B are perspective views of another embodiment of the present invention.
Figure 24B:
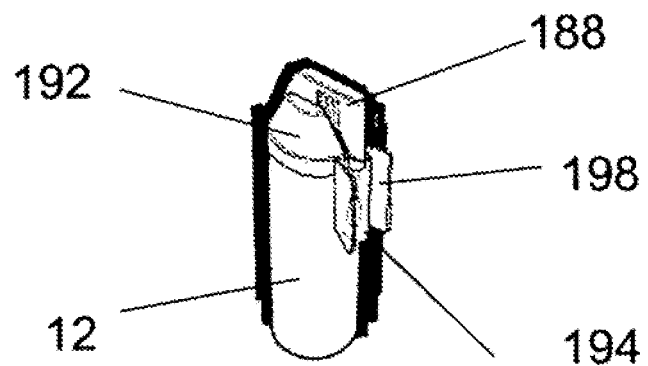

In the embodiment of FIGS. 24A and 24B, the applicator 18 is disposed in an actuator 188 in the same manner as the previous embodiments. A cap 192 is mounted to container 12. Actuator 188 is positioned within cap 192 to engage the outlet stem (not shown). Attached to cap 192 is a reservoir 194 for enclosing the applicator. A pair of cold shields 198 is attached to cap 192 and extend along either side of the reservoir.

Figures 25A, 25B:
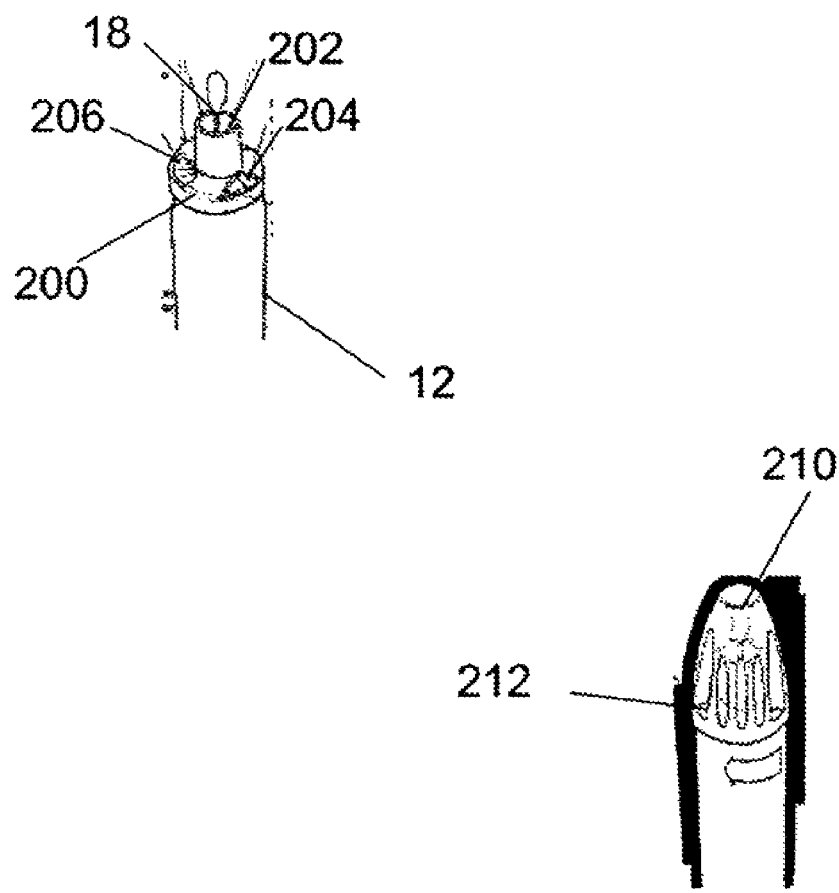
FIGS. 25A and 25B are perspective views of still another embodiment of the present invention.

As shown in FIGS. 25A and 25B, a cover 200 includes a reservoir 202 extending upwardly therefrom. Reservoir 202 extends around the outlet stem and applicator 18 communicates with the outlet stem of container 12. Cover 200 includes a plurality of apertures 204 spaced thereabout. Rotary wedge type actuators 206 are located within the vicinity of apertures 204 and our designed to be rotated to depress the valve of the outlet stem to dispense the cryogen into applicator tube 18. A shield 210 snaps over the container and cover. Shield 210 includes a plurality of lugs 212 that engage the rotary wedge actuators through apertures 204. When shield 210 is rotated the actuators are rotated to dispense the cryogen. Shield 210 prevents dispensing of the cryogen unless the device is assembled as shown.

In summary, each of the embodiments contains two or more parts that have to be correctly assembled for the device to work properly. One part will be the canister equipped with an appropriate fixture that is designed to interlock with the trigger portion of the device. That part may also be a dispensing head or trigger that is attached to the outlet tube from the canister. The dispensing head may have a fitting that allows the insertion of an applicator or may be a single unit containing an applicator.

In operation, the cap, shield and actuator with the applicator are preferably pre-assembled with propellant container 12. As discussed above, the tip is preferably permanently secured to the applicator tube. Thereafter, the actuator is pushed downward to open the valve and dispense cryogen from the container through a passageway within the actuator into the applicator tube. After dispensing, the actuator and applicator tube can be removed from the container and without removing the applicator from the actuator; the tip with the refrigerant contained therein is immediately applied to the wart for a period of, for example, twenty seconds, in order to freeze the wart.

Although the present invention has been described in relation to particular embodiments thereof, many other variations and modifications and other uses will become apparent to those skilled in the art. It is preferred therefore, that the present invention be limited not by the specific disclosure herein, but only by the appended claims.

What is claimed is:

1. A cryosurgery device for dispensing a liquid refrigerant from a container having a valve stem extending outwardly therefrom, the device comprising:
   an actuator adapted to seat on the valve stem of the container in order to depress the valve stem to release the liquid refrigerant from the container, said actuator including an inner passageway having opposed ends disposed therein, one of the ends of the passageway being in fluid communication with the valve stem;
   an applicator having first and second opposed ends, the first end being mounted to said actuator at the other end of the inner passageway and the second end of the applicator having a tip for receiving liquid refrigerant;
   shield means in communication with said actuator for removably receiving said actuator and for completely and removably receiving the applicator, the shield means being adapted to contain all dispensed liquid refrigerant that is not held within the applicator during dispensing; and
   means for interlocking said actuator and said shield means so that the liquid refrigerant can only be dispensed into the applicator when said actuator engages said shield means.

2. The device of claim 1, wherein said shield means comprises a cap mounted on the container, the actuator being removably disposed within the cap, and a sheath attached to the cap for removably receiving the applicator.

3. The device of claim 2, wherein the sheath and the cap are a single, unitary piece.

4. The device of claim 2, wherein the sheath is removably attached to the cap.

5. The device of claim 2, wherein said actuator comprises an actuator shell and an actuator insert disposed within the actuator shell.

6. The device of claim 5, wherein the inner passageway extends through the actuator insert.

7. The device of claim 6, wherein the interlocking means comprises a shoulder located within the inner passageway of the actuator insert, said shoulder engaging the valve stem to dispense the liquid refrigerant only when the actuator insert and the actuator shell are positioned within the cap.

8. The device of claim 5, wherein the cap includes a pair of spaced sidewalls, the actuator being disposed between said sidewalk.

9. The device of claim 8, wherein the cap includes a boss extending upwardly between the sidewalls, the valve stem of the container being surrounded by the boss.

10. The device of claim 2, wherein the cap includes a pair of spaced sidewalls, the actuator being disposed between said sidewalk.

11. The device of claim 7, wherein the cap includes a boss extending upwardly between the sidewalk, the valve stem of the container being surrounded by the boss.

12. The device of claim 2, wherein the interlocking means comprises a shoulder located within the end of the inner passageway of said actuator, said shoulder engaging the valve stem to dispense the liquid refrigerant only when said actuator is positioned within the cap.

13. The device of claim 2, wherein the sheath includes a reservoir disposed in a bottom portion thereof.

14. The device of claim 2, wherein the sheath includes at least one vent for releasing gas therefrom.

15. A method of dispensing liquid refrigerant from a cryosurgery device comprising the steps of:
   providing a container of liquid refrigerant having a valve stem extending outwardly therefrom;
   attaching an actuator mechanism to the container, said actuator mechanism including an inner passageway in fluid communication with the valve stem and an applicator;
   removably positioning the applicator within a shield device to contain all dispensed liquid refrigerant that is not held within the applicator;
   interlocking the actuator mechanism and the shield device, such that when said actuator mechanism is actuated refrigerant passes from the valve stem through the actuator mechanism and into the applicator; and
   applying a force to the actuator mechanism to dispense the refrigerant to a porous tip of the applicator.

16. The method of claim 15, further comprising the step of providing a cap on the container, the valve stem extending upwardly into said cap.

17. The method of claim 16, wherein the step of attaching the actuator mechanism comprises removably positioning the actuator mechanism between spaced sidewalk of said cap.

18. The method of claim 16, wherein the shield devise and the cap are formed as a single, unitary piece and the step of removably positioning the applicator within the shield device comprises positioning one end of the applicator within a first end of the inner passageway of the actuator mechanism and removably positioning the actuator mechanism into the cap while removably positioning the other end of the applicator into a sheath of the shield device.

19. The method of claim 18, wherein the step of interlocking said actuator mechanism and the shield device comprises positioning the valve stem of the container within a second end of the inner passageway, said second end including a shoulder that engages the valve stem to dispense the liquid refrigerant only when the actuator mechanism is positioned within said cap.

20. The method of claim 18, wherein the applicator is affixed to the first end of the inner passageway of the actuator mechanism prior to removably positioning the actuator within said cap.

21. The method of claim 16, wherein the step of attaching the actuator mechanism to the container comprises positioning an actuator insert within an actuator shell and removably positioning the actuator shell and the actuator insert within said cap.

22. A cryosurgery device for dispensing a liquid refrigerant from a container having a valve stem extending outwardly therefrom, the device comprising:
- an actuator for engaging a valve stem of the container in order to depress the valve stem to release the liquid refrigerant from the container, said actuator including an inner passageway having opposed first and second ends disposed therein, the first end of the passageway being in fluid communication with the valve stem;
- an applicator tube affixed to the second end of the inner passageway, the applicator tube having a tip for receiving liquid refrigerant;
- a shield mechanism in communication with said actuator for removably receiving said actuator and for completely and removably receiving the applicator tube, the shield mechanism being adapted to contain all dispensed liquid refrigerant that is not held within the applicator tip during dispensing; and
- means for interlocking said actuator and said shield mechanism so that the liquid refrigerant can only be dispensed into the applicator when said actuator engages said shield mechanism.

23. The device of claim 22, wherein said shield mechanism comprises a cap disposed on the container for removably receiving the actuator and a sheath for removably receiving the applicator tube formed as a single, unitary piece with said cap.

24. The device of claim 23, wherein said interlocking means includes a shoulder disposed in the first end of the inner passageway of the actuator, wherein the liquid refrigerant can only be dispensed when said shoulder engages the valve stem when said actuator is positioned within said cap and said applicator tube is positioned within said sheath.

* * * * *